(12) United States Patent
McMahon et al.

(10) Patent No.: US 11,571,440 B2
(45) Date of Patent: Feb. 7, 2023

(54) DEFIBROTIDE FOR THE PREVENTION AND TREATMENT OF CYTOKINE RELEASE SYNDROME AND NEUROTOXICITY ASSOCIATED WITH IMMUNODEPLETION

(71) Applicant: JAZZ PHARMACEUTICALS IRELAND LIMITED, Dublin (IE)

(72) Inventors: Sarah McMahon, Palo Alto, CA (US); Yasuhiro Oki, Palo Alto, CA (US)

(73) Assignee: JAZZ PHARMACEUTICALS IRELAND LIMITED, Dublin (IE)

( * ) Notice: Subject to any disclaimer, the term of this patent is extended or adjusted under 35 U.S.C. 154(b) by 108 days.

(21) Appl. No.: 17/046,906

(22) PCT Filed: Apr. 12, 2019

(86) PCT No.: PCT/US2019/027210
§ 371 (c)(1),
(2) Date: Oct. 12, 2020

(87) PCT Pub. No.: WO2019/200251
PCT Pub. Date: Oct. 17, 2019

(65) Prior Publication Data
US 2021/0187004 A1 Jun. 24, 2021

Related U.S. Application Data

(60) Provisional application No. 62/753,711, filed on Oct. 31, 2018, provisional application No. 62/657,161, filed on Apr. 13, 2018, provisional application No. 62/656,486, filed on Apr. 12, 2018.

(51) Int. Cl.
| | | |
|---|---|---|
| A61K 31/711 | (2006.01) |
| G01N 33/68 | (2006.01) |
| A61P 25/00 | (2006.01) |

(52) U.S. Cl.
CPC ............ *A61K 31/711* (2013.01); *A61P 25/00* (2018.01); *G01N 33/6896* (2013.01); *G01N 2800/52* (2013.01)

(58) Field of Classification Search
CPC .......... A61K 2039/5158; A61K 31/711; C07K 2319/03; G01N 33/574
See application file for complete search history.

(56) References Cited

PUBLICATIONS

Bonomini et al. (Nephron, 1985 vol. 40:195-200).*
Johnson et al. (The Annals of Pharmacotherapy, Apr. 1994, vol. 28:460-463).*
Summary of Product Characteristics for Defitelio, Oct. 18, 2013.*
Jazz Pharmaceuticals, Clinical Trial NCT0354106, first posted May 17, 2019.*

(Continued)

*Primary Examiner* — Terra C Gibbs
(74) *Attorney, Agent, or Firm* — Cooley LLP

(57) ABSTRACT

The present disclosure provides method of preventing, lessening the effects, or treating cytokine release syndrome (CRS) or related disorders, and/or neurotoxicity associated with immunotherapy comprising administering defibrotide. The defibrotide can be administered after the immunotherapy begins or be administered prophylactically before immunotherapy begins or before the patient develops CRS and/or neurotoxicity.

17 Claims, 10 Drawing Sheets

(56) References Cited

PUBLICATIONS

Fundacion para la Formacion e Investigacion Sanitarias de la Region de Murcia, Clinical Trial NCT04348383, first posted Apr. 16, 2020.*

Jazz Pharmaceuticals News Release, Oct. 10, 2019.*

Benimetskaya et al., "Angiogenesis alteration by defibrotide: implications for its mechanism of action in severe hepatic veno-occlusive disease," Blood, vol. 112, No. 10, Nov. 15, 2008, pp. 4343-4352.

Beşişik al., "Complete resolution of transplantation-associated thrombotic microangiopathy and hepatic veno-occlusive disease by defibrotide and plasma exchange," Turk J Gastroenterol 2005, 16(1): 34-37.

Corbacioglu et al., "Defibrotide for the Treatment of Hepatic Veno-Occlusive Disease: Final Results From the International Compassionate-Use Program," Biol Blood Marrow Transplant (2016) 22: 1874-1882.

International Search Report and Written Opinion of the International Searching Authority for International Application No. PCT/US2019/027210 dated Jul. 4, 2019, 12 pages.

Mitsiades et al., "Defibrotide (OF), an Orally Bioavailable Modulator of Myeloma Tumor-Microenvironment Interactions: Molecular Sequelae and Clinical Implications," Blood, 2006, 108: 3523, 6 pages.

Sala et al., "Polydeoxyribonucleotide (defibrotide) protects against post-ischemic behavioral, electroencephalographic and neuronal damage in the gerbil," European Journal of Pharmacology (1997) 328: 143-152.

Vangelista et al., "Effects of Defibrotide in Acute Renal Failure due to Thrombotic Microangiopathy," Haemostasis (1986) 16: Suppl. 1, pp. 51-54.

* cited by examiner

A

B ial Application PCT/US2019/027210, filed Apr. 12, 2019, which claims priority to U.S. Provisional Application 62/656,486, filed Apr. 12, 2018; U.S. Provisional 62/657, 161, filed Apr. 13, 2018; and U.S. Provisional 62/753,711, filed Oct. 31, 2018, the contents of each of which are herein incorporated by reference in their entireties.

DEFIBROTIDE FOR THE PREVENTION AND TREATMENT OF CYTOKINE RELEASE SYNDROME AND NEUROTOXICITY ASSOCIATED WITH IMMUNODEPLETION

This application is a 371 National Stage Entry of International Application PCT/US2019/027210, filed Apr. 12, 2019, which claims priority to U.S. Provisional Application 62/656,486, filed Apr. 12, 2018; U.S. Provisional 62/657, 161, filed Apr. 13, 2018; and U.S. Provisional 62/753,711, filed Oct. 31, 2018, the contents of each of which are herein incorporated by reference in their entireties.

FIELD

The present disclosure is directed to methods of administering defibrotide to prevent and/or treat cytokine release syndrome (CRS) and/or neurotoxicity, especially that associated with CAR-T or bispecific antibody therapy.

BACKGROUND

Immunotherapy, including the use of lymphodepletion or monoclonal antibodies, has become an important tool in the treatment of cancer and neoplasms. T cells expressing chimeric antigens (CAR-T cells) and bispecific antibodies are becoming an option for lymphodepletion. However, while these therapies show promise, treatment with the CAR-T cells or bispecific antibodies may lead to a large, rapid release of cytokines into the blood and cause cytokine release syndrome (CRS) or CAR-T cell related encephalopathy syndrome (CRES) [also referred to herein as CAR-T associated neurotoxicity or ICANS (immune effector cell (IEC) therapy associated neurotoxicity syndromes)].

CRS is characterized by high fever, hypotension, hypoxia, and/or multi-organ toxicity, and can lead to death. Rarely, CRS can evolve into fulminant hemophagocytic lymphohistiocytosis (HLH), which is characterized by severe immune activation, lymphohistiocytic tissue infiltration and immune-mediated multi-organ failure associated with severe pancytopenia. Neurotoxicity is characterized by damage to nervous tissue that can lead to tremors, encephalopathy, dizziness, or seizures.

In a pivotal multicenter ZUMA-1 trial of Axi-cel in one hundred and one adult patients with refractory aggressive B-cell NHL, the rates of grade ≥3 CRS and CRES were 13% and 28% respectively. Additionally, in the JULIET trial of tisagenlecleucel in ninety-three adult patients with relapsed or refractory DLBLC, these rates were 22% and 12% respectively (Schuster, S., et al., N. Eng. J. Med. (2019); 380:45-56).

The present disclosure is directed to methods of administering defibrotide to prevent and/or treat cytokine release syndrome (CRS), especially CRS associated with CAR-T therapy.

SUMMARY OF THE INVENTION

Figure 1:
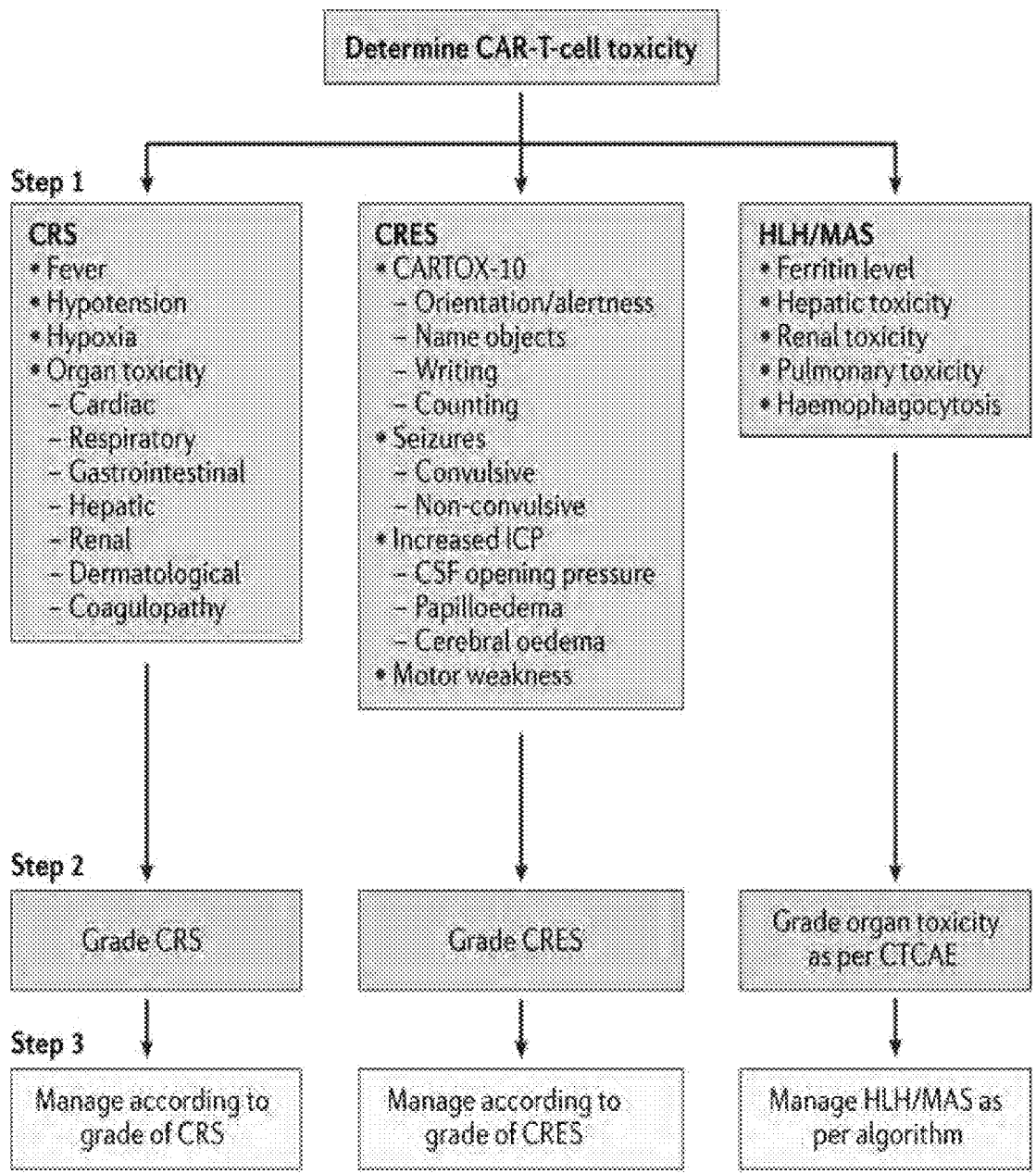
FIG. 1 shows a summary algorithm of evaluation and treatment of CAR-T related toxicities as categorized prior to December 2018.
Figure 2:
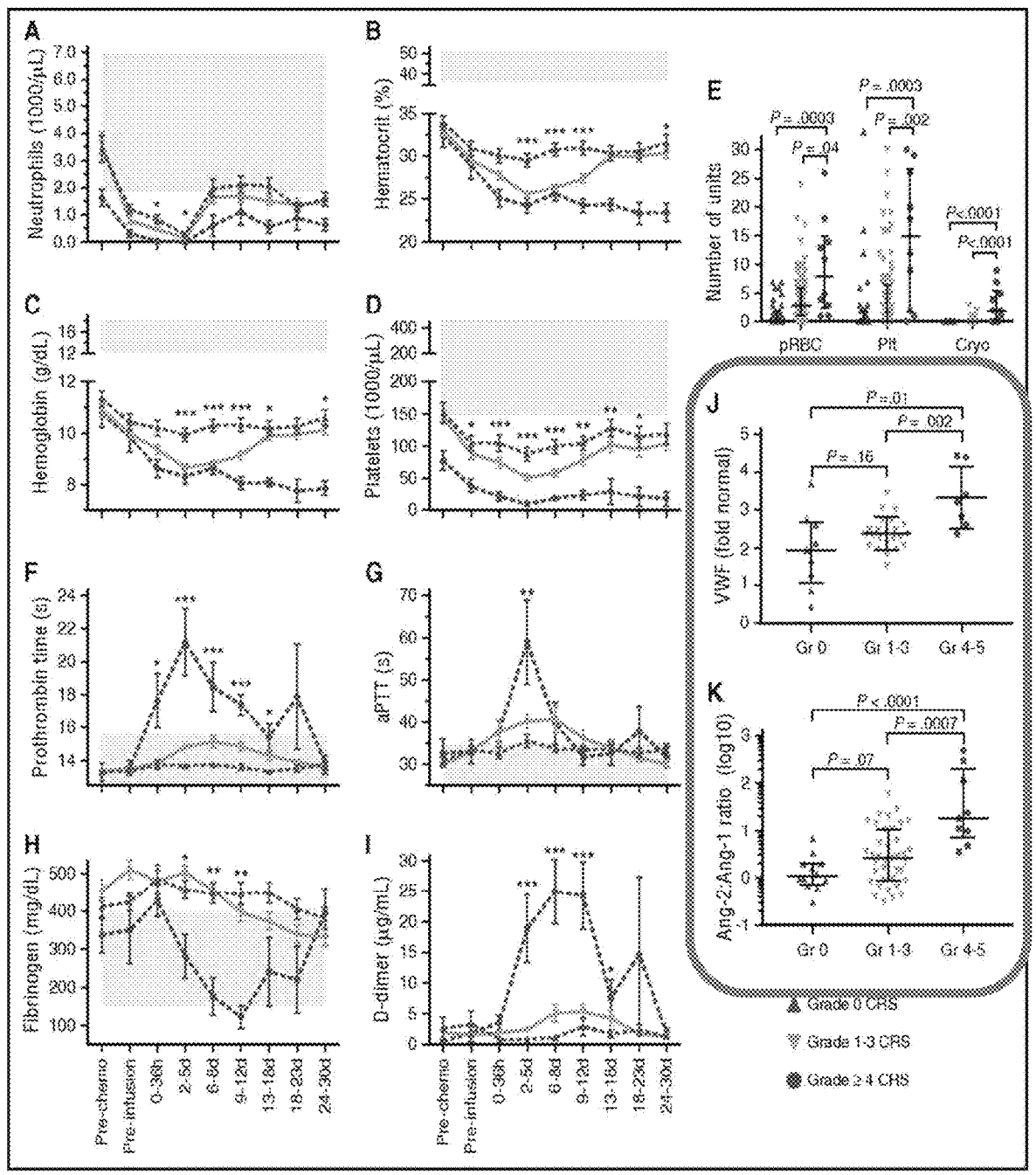
FIG. 2A-K shows changes in the serum cytokine levels during treatment per CRS grade
Figure 3:
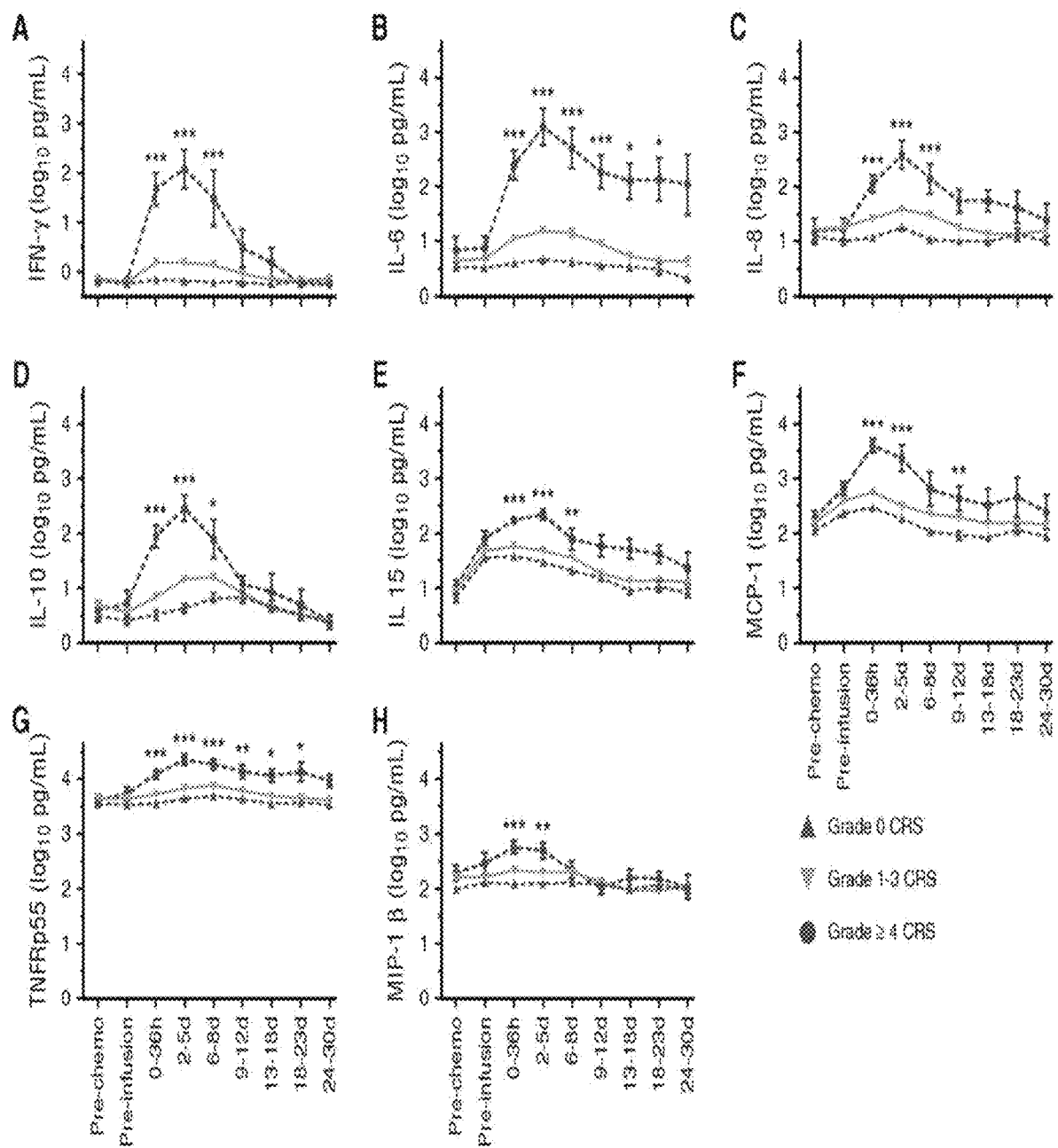
FIG. 3A-H shows changes in the serum cytokine levels during treatment per CRS grade.
Figure 4:
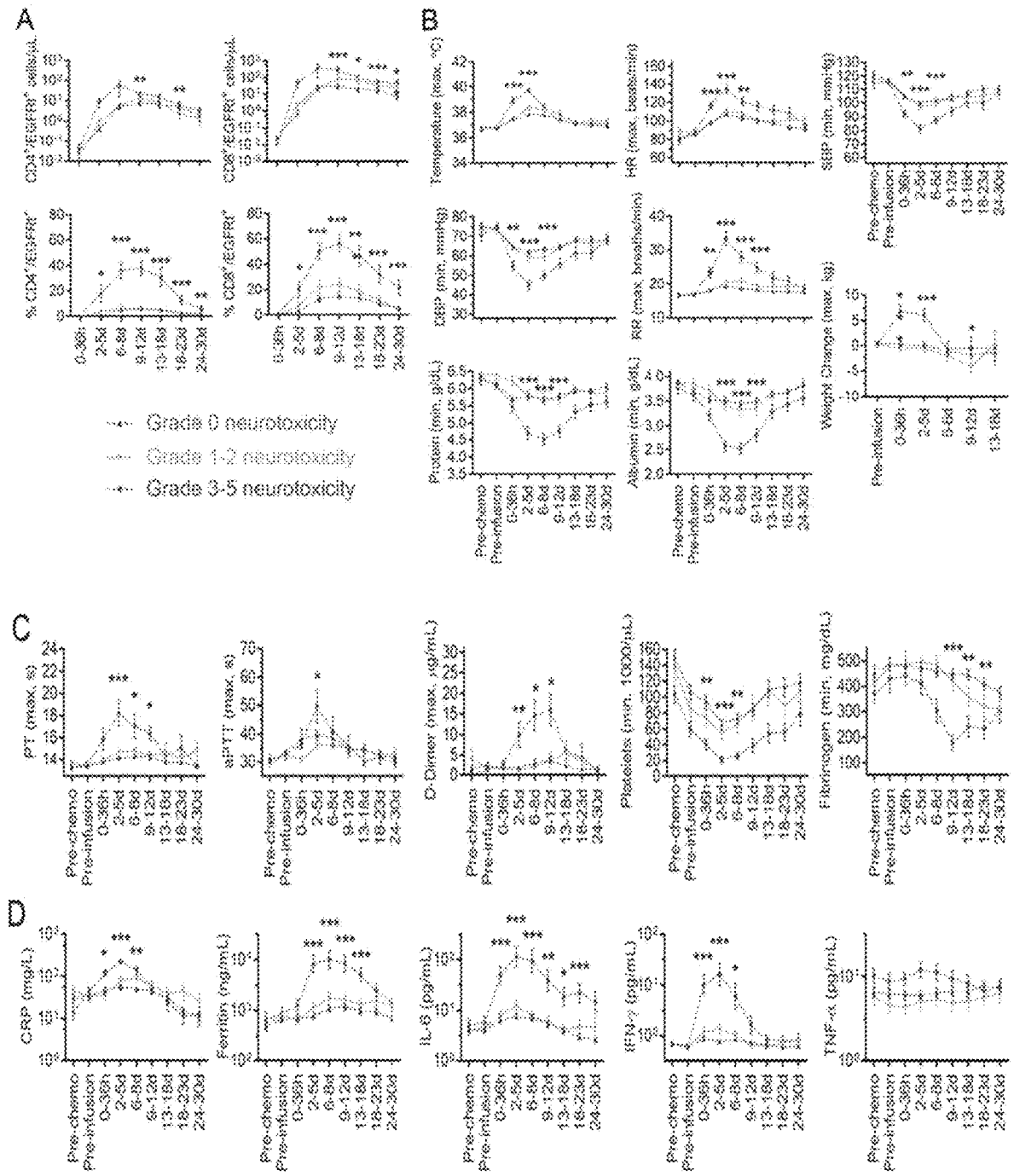
FIG. 4A-D shows changes in the serum cytokine levels during treatment per CRES (or CAR-T associated neurotoxicity) grade.
Figure 5:
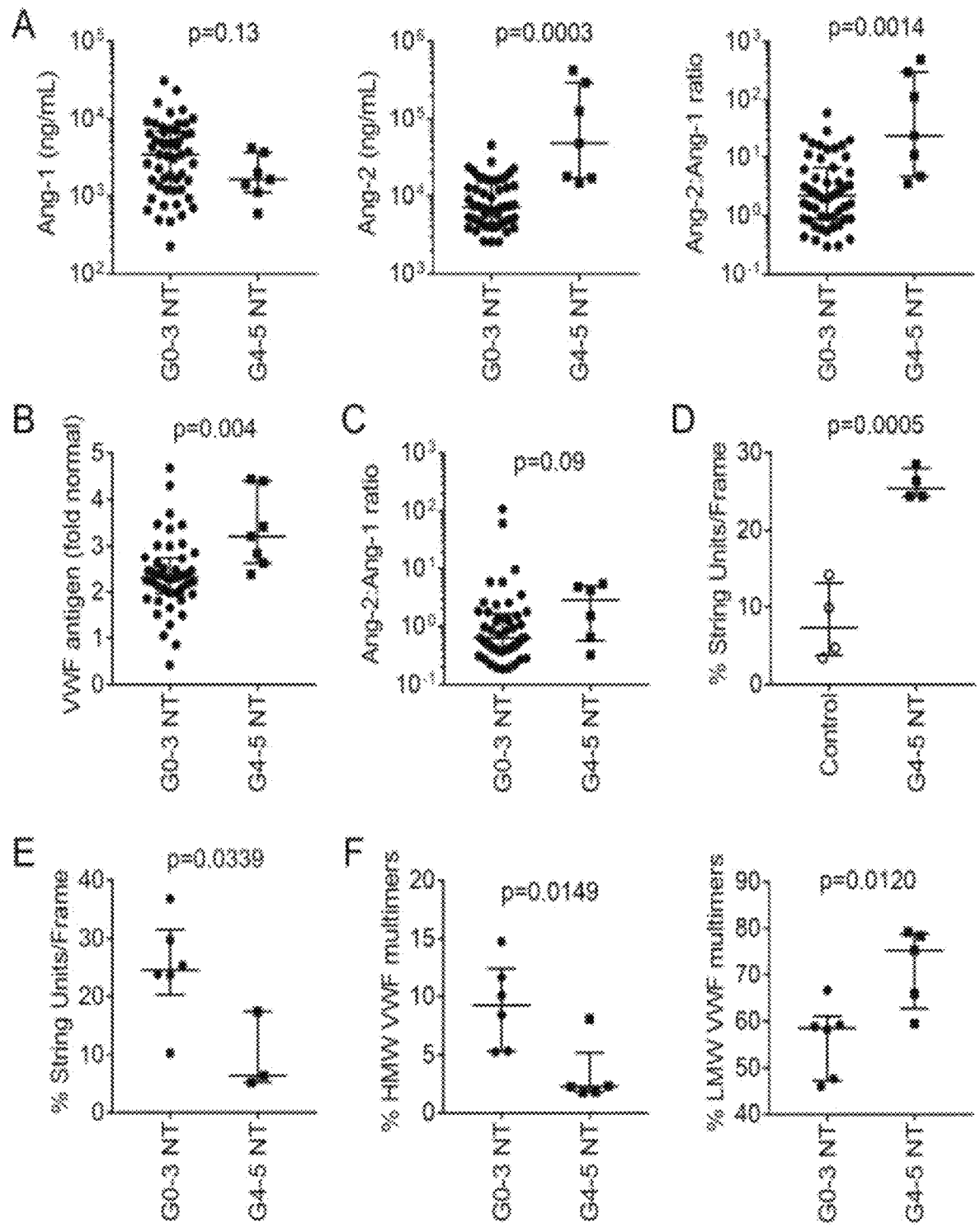
FIG. 5A-G shows changes in the serum cytokine levels during treatment per CRES (or CAR-T associated neurotoxicity) grade.
Figure 6:
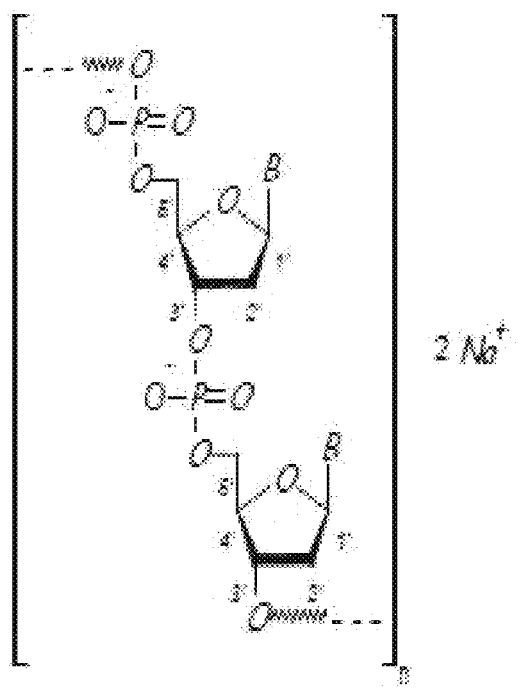
FIG. 6 shows the structure of defibrotide.
Figure 6:
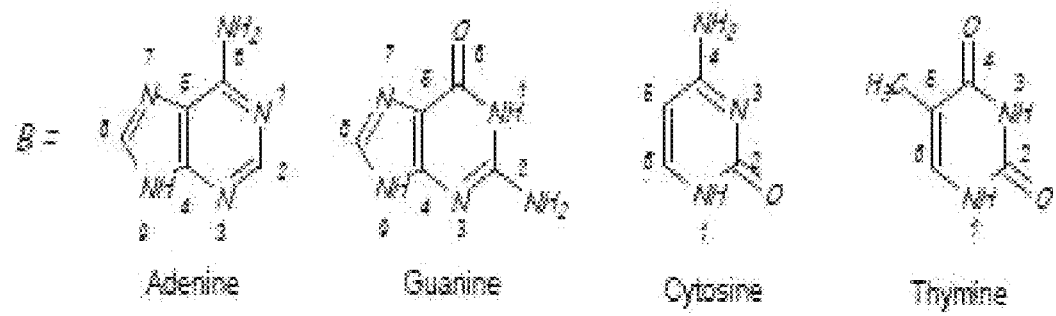
Figure 7:
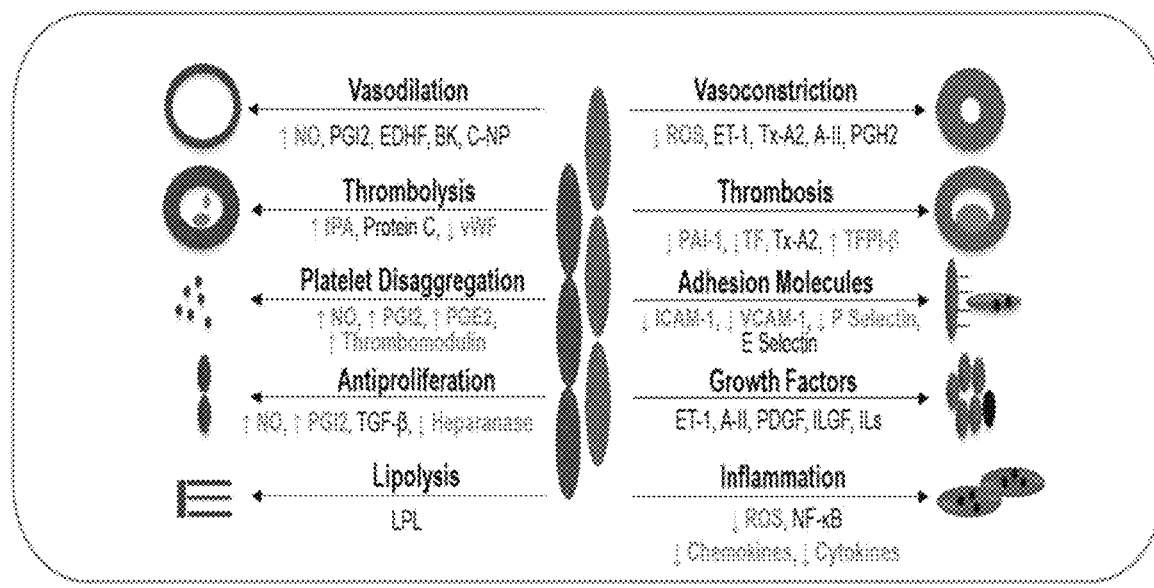
FIG. 7A-B shows representative mechanisms of action for defibrotide.
Figure 7:
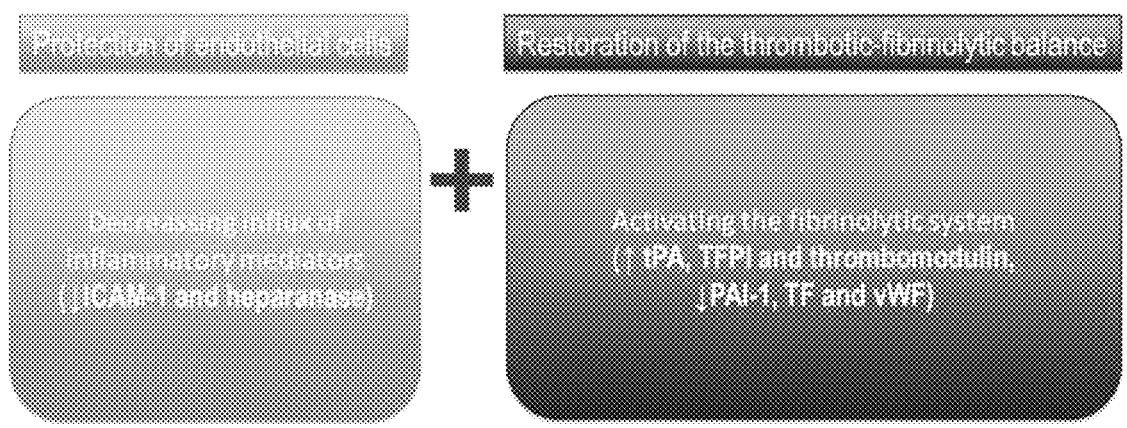
Figure 8:
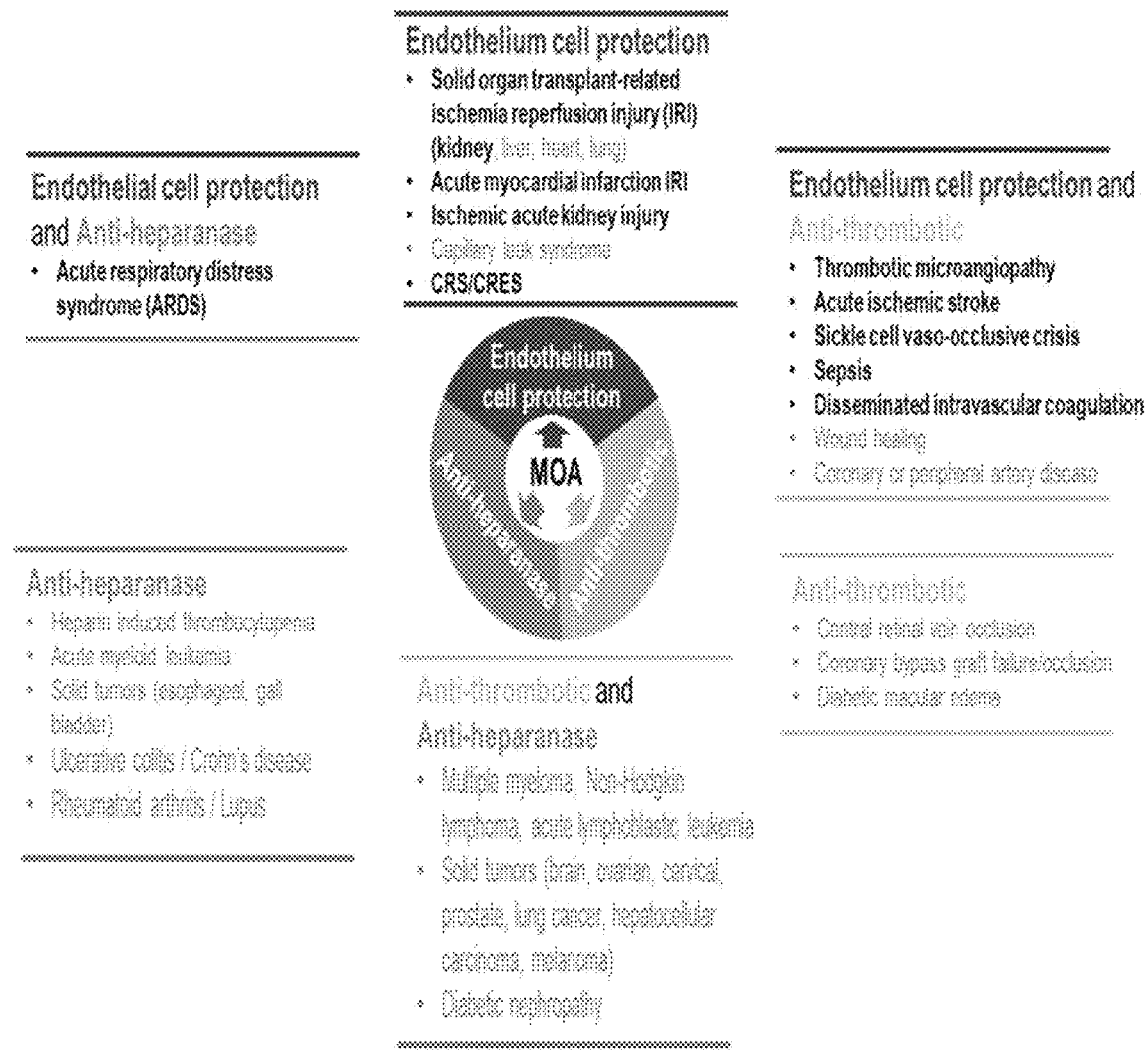
FIG. 8 shows representative effects of defibrotide on epithelial cells.

In some aspects, the present disclosure provides methods of preventing, lessening the effects, or treating Cytokine Release Syndrome (CRS) in a patient comprising administering a therapeutically effective amount of defibrotide. In some embodiments, the patient is receiving or about to receive an immunotherapy. In some embodiments, the immunotherapy is a lymphodepletion chemotherapy. In some embodiments, the lymphodepletion chemotherapy is a CAR-T therapy. In some embodiments, the immunotherapy is a monoclonal antibody. In some embodiments, the immunotherapy is a bispecific antibody.

In some embodiments, the present disclosure provides methods of preventing, lessening the effects, or treating CAR-related encephalopathy syndrome (CRES) (i.e. CAR-T associated neurotoxicity/ICANS) in a patient comprising administering a therapeutically effective amount of defibrotide.

In some embodiments, the present disclosure provides methods of preventing, lessening the effects, or treating neurotoxicity in a patient comprising administering a therapeutically effective amount of defibrotide.

In some embodiments, the present disclosure provides methods of decreasing serum biomarker levels associated with the development of CRS and/or CRES (i.e. CAR-T associated neurotoxicity/ICANS), in a patient comprising administering a therapeutically effective amount of defibrotide. In some embodiments, the defibrotide is administered to the patient until the serum biomarker levels decrease to levels observed in patients who do not develop CRS and/or CRES (i.e. CAR-T associated neurotoxicity/ICANS). In some embodiments, the defibrotide is administered to the patient until the serum biomarker levels decrease to levels observed in the same patient before immunotherapy treatment. In some embodiments, the biomarker is selected from the group consisting IL1-Rα, IL-6, IL-6R, soluble IL-6R, soluble gp130, IFNα, IFNγ, IL-15, IL-8, IL-2, sIL2Ra, IL8, IP10, MCP1, MIG, GM-CSF, TNFα, MIP-1α, MIP1β and IL-10, anti-neuron autoantibodies, stress proteins (e.g. heat shock proteins), MAO and ChE enzyme activity, other serum endothelial biomarkers such as vWF, ANG2; D2 receptor, mACh receptor, Hsp70, autoantibodies, c-fos expression, ornithine decarboxylase gene expression, cerebrospinal fluid markers, and/or plasma components (e.g. myelin basic protein, anti-NF, anti-myelin antibody, anti-GFAP antibody, anti-nerve growth factor antibody), IFNg, TNFRp55, Endothelin-1, soluble Vascular Cell Adhesion Molecule (VCAM), Intra-Cellular Adhesion Molecule (ICAM), E-selectin, soluble Thrombomodulin, Von Willebrand factor (vWF), DAMP (damage-associated molecular patterns), and PAMP (pathogen-associated molecular patterns) or a combination thereof.

In some embodiments, the present disclosure provides methods of determining whether to administer defibrotide to a patient receiving or about to receive an immunotherapy comprising: a) determining the expression of a biomarker associated with CRS, or CRES (i.e. CAR-T associated neurotoxicity/ICANS) in the patient; and b) administering a therapeutically effective amount of defibrotide.

In some embodiments, the defibrotide is administered before the administration of the immunotherapy. In some embodiments, the defibrotide is administered at the same time as the administration of the immunotherapy. In some embodiments, the defibrotide is administered on the same day as the administration of the immunotherapy. In some embodiments, the defibrotide is administered after the administration of the immunotherapy.

In some embodiments, the defibrotide is administered each day of lymphodepletion. In some embodiments, the lymphodepletion occurs before a CAR-T infusion. In some embodiments, the defibrotide is administered on the day CAR-T infusion commences (e.g. the first day of CAR-T infusion). In some embodiment, the defibrotide is administered for at least two days after the CAR-T infusion. In some embodiments, the defibrotide is administered starting on the day CAR-T infusion commences and for at least two days afterward.

In some embodiments, the defibrotide is administered before the development of CRS, CRES (i.e. CAR-T associated neurotoxicity/ICANS) or symptoms thereof. In some embodiments, the defibrotide is administered after the development of CRS, CRES (i.e. CAR-T associated neurotoxicity/ICANS) or symptoms thereof. In some embodiments, the defibrotide is administered to patients at risk of developing CRS, and/or CRES (i.e. CAR-T associated neurotoxicity/ICANS) after administration of immunotherapy.

In some embodiments, the defibrotide is administered between one and three days before administration of the immunotherapy begins. In some embodiments, the defibrotide is administered between one and three days before administration of the immunotherapy begins, and continues for up to 30 days.

In some embodiments, the defibrotide is administered after the development of CRS, CRES (i.e. CAR-T associated neurotoxicity/ICANS) or symptoms thereof and administration continues until symptoms improve.

In some embodiments, the defibrotide is administered at a dose between 1 mg/kg and 10 mg/kg. In some embodiments, the defibrotide is administered at a dose of 6.25 mg/kg.

In some embodiments, the defibrotide is administered once a day. In some embodiments, the defibrotide is administered in multiple doses per day. In some embodiments, the defibrotide is administered in two to ten doses per day. In some embodiments, the defibrotide is administered four times a day. In some embodiments, the defibrotide is administered every six hours.

In some embodiments, the defibrotide is administered intravenously, every six hours at a dose of 6.25 mg/kg.

DETAILED DISCLOSURE

Definitions

As used herein, the term "nucleic acid" includes "nucleic acids and their salts" and refers to molecules which are comprised of nucleotides, including polymers or large biomolecules composed of nucleotide units linked together in a chain; this includes polynucleotides and oligonucleotides including those comprised of ribose and/or deoxyribose monomers; they can be uniform in size and/or sequence or they can be polydisperse; they can be of any length, including a mixture of different lengths, but some embodiments are generally between 10-400 bases, 20-200 bases, or 45-60 bases long; in some embodiments the mean MW is between 13 and 20 kilodaltons ("kDa"); they can be single or double stranded, but some embodiments are mostly single stranded polydeoxyribonucleotide salts within the limits stated elsewhere in this application. This also includes DNA sequences that are obtained from the controlled depolymerization of animal intestinal mucosal genomic DNA and, as one embodiment, includes defibrotide.

The term defibrotide identifies a polydeoxyribonucleotide that is obtained by extraction from animal and/or vegetable tissues but which may also be produced synthetically; the polydeoxyribonucleotide is normally used in the form of an alkali-metal salt, generally a sodium salt, and generally has a molecular weight of 13 to 30 kDa (CAS Registry Number: 83712-60-1). Preferably, defibrotide is obtained according to U.S. Pat. Nos. 4,985,552 and 5,223,609 and/or presents the physical/chemical characteristics described in the same U.S. Pat. Nos. 4,985,552 and 5,223,609, herein incorporated by reference. More in particular, defibrotide is a mixture of polydeoxyribonucleotides having formula of random sequence: P1-5, $(dAP)_{12-24}$, $(dGP)_{10-20}$, $(dPp)_{13-26}$, $(dCP)_{10-20}$, where: P=phosphoric radical; dAp=deoxyadenylic monomer; dGp=deoxyguanylic monomer; dTp=deoxythymidinic monomer; dCp=deoxycytidynic monomer; and/or shows the following chemical/physical characteristics: electrophoresis=homogeneous anodic mobility, and/or extinction coefficient, $E_1$ $cm^{1\%}$ at 260±1 nm nm=220±10, and/or $E_{230}/E_{260}$=0.45±0.04, and/or coefficient of molar extinction (referred to phosphorous) $\epsilon(P)$=7.750±500, and/or rotatory power $[\alpha]_D^{20°}$=53°±6; and/or reversible hyperchromicity, indicated as % in native DNA and/or h=15±5.

As used herein, the term "defibrotide" refers to both natural and synthetic sources of defibrotide, including synthetic phosphodiester oligonucleotides as described in US patent application number 20110092576.

Other uses of defibrotide, methods for its production and testing are described in the following patents, patent applications and articles, each of which is hereby incorporated by reference in its entirety: U.S. Pat. Nos. 3,770,720; 3,829,567; 3,899,481; 4,693,134; 4,693,995; 4,938,873; 4,985,552; 5,081,109; 5,116,617; 5,223,609; 5,646,127; 5,646,268; 5,977,083; 6,046,172; 6,699,985; 6,767,554; 7,338,777; 8,551,967; 8,771,663, 9,902,952; US Patent Publication Nos. 20080194506; 20090131362; 20110092576; 20130231470; 20140005256, U.S. patent application Ser. Nos. 14/019,674; 14/323,918; 14/408,272; and International applications WO 2013/190582 and PCT/EP2015/077355. See also Palmer and Boa, Defibrotide. A Review of its pharmacodynamic and pharmacokinetic properties, and therapeutic use in vascular disorders, Drugs, 1993, February; 45(2):259-94; which is incorporated by reference herein. Other references cited throughout are also incorporated by reference in their entireties.

The term, "glycylglycine" or "Gly-Gly" or "GlyGly" or "glygly" as used herein, refers to a simple peptide, made of two glycine molecules (glycine is a simple, nonessential amino acid); the dipeptide is used in the synthesis of more complicated peptides. Glycylglycine, an ampholyte, is also sometimes referred to as Diglycine, Diglycocoll, Glycine dipeptide, N-Glycylglycine. It can be made by methods such as those described in CN patent application 101759767 which is incorporated herein by reference in its entirety.

The term, "excipient," as used herein, refers to any substance that may be formulated with defibrotide and may be included for the purpose of enhancement of the defibrotide in the final dosage form, such as facilitating its bioavailability, reducing viscosity and/or osmolality, enhancing solubility of the composition or to enhance long-term stability. Excipients can also be useful in the manufacturing process, to aid in the handling of the active substance. The selection of appropriate excipients also depends upon the route of administration and the dosage form, as well as the active ingredient and other factors. Accordingly, defibrotide may be combined with any excipient(s) known in the art that allows tailoring its performance during manufacturing or administration as well as its in vitro and in vivo performance. Many of these excipients may be utilized to tailor the pharmacokinetic profiles of defibrotide formulations.

The term, "buffer" or "buffering agent," as used herein, refers to a solution which resists changes in the hydrogen ion concentration on the addition of a small amount of acid or base. This includes, for example, a weak acid or base that is used to maintain the pH of a solution near a chosen pH value after the addition of another acidic or basic compound. The function of such buffer or buffering agent is to prevent a change in pH of a solution when acids or bases are added to said solution.

The term, "pH adjusting agent," as used herein, refers to an acid or base used to alter the pH of a solution to a chosen pH value. The function of such an agent is to alter the pH of a solution to the desired value subsequent to the addition of acidic or basic compounds.

The term, "formulation," as used herein, refers to compositions for therapeutic use, including, for example, a stable and pharmaceutically acceptable preparation of a pharmaceutical composition or formulation disclosed herein.

The terms, "low-viscosity formulation," or "low viscosity formulation," as used herein, refers to a formulation which has a viscosity that is less than about 70 centipoise (cP). Normally viscosity is measured at ambient/room temperatures of (e.g. 15° C. to 35° C.; between 18° C. to 25° C. or between 21° C. to 23° C.) depending on the geographic region and/or weather conditions of the room in which it is being measured.

The term, "aqueous formulation," as used herein, refers to a water-based formulation, in particular, a formulation that is an aqueous solution.

The term, "high concentration formulation" or "high concentration liquid formulation" or "HCLF" as used herein, refers to those formulations where the concentration of the nucleic acid is about 80 mg/mL or higher; or about 85 mg/mL or higher.

The term, "high concentration defibrotide formulations" as used herein, refers to those formulations where the defibrotide concentration is about 80 mg/mL or higher, or about 85 mg/mL or higher.

The term, "pharmacokinetic" or "PK" as used herein, refers to in vivo movement of an individual agent in the body, including the plasma concentration time profiles and kinetic parameters like the maximum concentration (Cmax), area under the curve (AUC), and time to maximum concentration of said agent (Tmax).

The phrase "pharmaceutically acceptable" or "acceptable", as used in connection with compositions of the disclosure, refers to molecular entities and other ingredients of such compositions that are physiologically tolerable and do not typically produce untoward reactions when administered to an animal and/or human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "physiologically relevant" as used herein, refers to a measurement, level or amount that is suitable for use in a pharmaceutical, therapeutic or other dosage form to be administered to an animal subject, particularly a human subject.

As used herein, the term "parenteral" refers to any non-oral means of administration. It includes intravenous (i.v. or IV) infusion, IV bolus injection, subcutaneous (s.c. or SC) and intramuscular (i.m. or IM) injection.

Throughout the present specification, the terms "about" and/or "approximately" may be used in conjunction with numerical values and/or ranges. The term "about" is understood to mean those values near to a recited value. For example, "about 1200 [units]" may mean within ±10% of 1200, within ±10%, ±9%, ±8%, ±7%, ±7%, ±5%, ±4%, ±3%, ±2%, ±1%, less than ±1%, or any other value or range of values therein. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

In certain embodiments, the defibrotide to be evaluated by the methods described herein are manufactured by a process such as that described in U.S. Pat. Nos. 4,985,552 and 5,223,609, both of which are hereby incorporated by reference in their entireties. In one preferred embodiment of the invention, defibrotide is a polydeoxyribonucleotide corresponding to the following formula of random sequence:

$$P_{1-5}, (dAp)_{12-24}, (dGp)_{10-20}, (dTp)_{13-26}, (dCp)_{10-20}$$

wherein: P=phosphoric radical
dAp=deoxyadenylic monomer
dGp=deoxyguanylic monomer
dTp=deoxythymidylic monomer
dCp=deoxycytidylic monomer The defibrotide as used herein may have one or more or all of the following chemico-physical properties: electrophoresis=homogeneous anodic mobility; extinction coefficient, E1 cm1% at 260±1 nm=220±10; extinction ratio, E230/E260=0.45±0.04; coefficient of molar extinction (referred to phosphorus), E(P)=7.750±500; rotary power

[α]D20°=53°±6; reversible hyperchromicity, indicated as % in native DNA, h=15±5; and a purine:pyrimidine ratio of 0.95±0.5.

In some aspects, the defibrotide is a high concentration, low viscosity defibrotide formulation. In some embodiments, the high concentration, low viscosity defibrotide formulation is one disclosed in U.S. application Ser. No. 16/105,319 filed Aug. 3, 2018 the contents of which are incorporated herein for all purposes.

In particular, defibrotide which may be administered subcutaneously and/or which may require less frequent dosing than defibrotide products currently on the market are provided. In some embodiments, a device used to administer defibrotide is one disclosed in U.S. Application No. 62/776,500 filed Dec. 7, 2018 the contents of which are incorporated herein for all purposes. In some embodiments, a device used to administer defibrotide is one disclosed in U.S. Application No. 62/802,099 filed Feb. 6, 2019 the contents of which are incorporated herein for all purposes. In certain embodiments, high concentration defibrotide formulations are self-administered on an out-patient basis (e.g. using an automated injection device of the instant disclosure). Some formulations of the disclosure have thixotropic and sheer thinning behaviors which are particularly preferred for subcutaneous and/or intramuscular administration. Formulations as provided herein offer improved tolerability, patient convenience during treatment and opportunity for outpatient dosing in comparison to currently available commercial nucleic acid formulations. In some embodiments, the viscosity of high concentration defibrotide formulations provided herein decreases over time. In certain embodiments, the viscosity and/or fluidity of high concentration defibrotide formulations provided herein decreases under an increase in shear strain. In certain embodiments, the viscosity and/or fluidity of high concentration defibrotide formulations decreases with increases in temperature. It should be understood that such properties are preferable for injectables and delivery devices, such as a syringe or preloaded subcutaneous device, in which the strain or shear stress the formulation is exposed to increases as the formulation passes from the barrel of the syringe/device through to the reduced orifice of the needle.

In some embodiments, the formulation comprises defibrotide in an amount between about 100 mg/mL to about 400 mg/mL, glycylglycine at a concentration of between about 5 mM and about 60 mM. In some embodiments, the high concentration low viscosity formulation further comprises sodium citrate. In some embodiments, the sodium citrate is present at a concentration of between about 10 mM to about 34 mM.

Other excipients can be added to the present formulations, such as preservatives, salts, or pH adjusting agents.

In some embodiments of the disclosure, the viscosity of the low-viscosity formulation is between about 1 to about 70 cP. In some embodiments, the viscosity of the low-viscosity formulation is between about 5 cP to about 70 cP, or about 10 cP to about 65 cP. In some embodiments, the viscosity of the low-viscosity formulation is about 5 cP, about 10 cP, about 15 cP, about 20 cP, about 25 cP, about 30 cP, about 35 cP, about 40 cP, about 45 cP, about 50 cP, about 55 cP, about 60 cP, about 65 cP, or about 70 cP.

In some embodiments, the low-viscosity formulations of the present disclosure have an osmolality between about 200 mOsm/kg and about 1000 mOsm/kg. In some embodiments, the low-viscosity formulations of the present disclosure have an osmolality between about 240 mOsm/kg to about 600 mOsm/kg or about 300 mOsm/kg to about 550 mOsm/kg. In some embodiments, the low-viscosity formulations of the present disclosure have an osmolality of about 200 mOsm/kg, about 240 mOsm/kg, about 250 mOsm/kg, about 300 mOsm/kg, about 350 mOsm/kg, about 400 mOsm/kg, about 450 mOsm/kg, about 500 mOsm/kg, about 600 mOsm/kg, about 650 mOsm/kg, about 700 mOsm/kg, about 750 mOsm/kg, about 800 mOsm/kg, about 850 mOsm/kg, about 900 mOsm/kg, or about 950 mOsm/kg.

In some embodiments, the formulation comprises between 100 mg/mL to about 400 mg/mL of defibrotide, and glycylglycine at a concentration of between about 5 mM and about 60 mM, wherein the formulation has a viscosity between about 5 and about 70 cP when measured at between 15° C. and 25° C., and an osmolality between about 240 mOsm/kg and about 700 mOsm/kg. In some embodiments, the high concentration low viscosity formulation further comprises sodium citrate. In some embodiments, the sodium citrate is present at a concentration of between about 10 mM to about 34 mM.

As used herein, the term "polydeoxyribonucleotide" refers to a polymer whose constituent monomer is a deoxyribonucleotide.

Subjects to be treated by the methods of the disclosed embodiments include both human subjects and animal subjects (e.g., dog, cat, monkey, chimpanzee, and/or the like) for veterinary purposes. The subjects may be male or female and may be any suitable age, e.g., neonatal, infant, juvenile, adolescent, adult, or geriatric. In some embodiments, the subjects are preferably mammalian.

The terms "a" and "an," when used to modify the ingredient of a composition, such as, active agent, buffering agent, and osmolyte, do not denote a limitation of quantity, but rather denote the presence of at least one of the referenced item. The term "or" or "and/or" is used as a function word to indicate that two words or expressions are to be taken together or individually. The terms "comprising," "having," "including," and "containing" are to be construed as open-ended terms (i.e., meaning "including, but not limited to"). The endpoints of all ranges directed to the same component or property are inclusive and independently combinable.

Throughout the present specification, the terms "about" and/or "approximately" may be used in conjunction with numerical values and/or ranges. The term "about" is understood to mean those values near to a recited value. For example, "about 1200 [units]" may mean within ±10% of 1200, within ±10%, ±9%, ±8%, ±7%, ±7%, ±5%, ±4%, ±3%, ±2%, ±1%, less than ±1%, or any other value or range of values therein. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

Cytokine Release Syndrome

Cytokine release syndrome is a form of systemic inflammatory response syndrome that arises as a complication of some diseases or infections, and is also an adverse effect of monoclonal antibody drug or bispecific antibody drug administration, and adoptive T-cell therapies such as CAR-T.

Without being bound by theory, CRS is triggered by the activation of T cells on engagement of their TCRs or CARs with cognate antigens expressed by tumor cells. The activated T-cells release cytokines and chemokines (including IL-2, soluble IL-2Ra, IFNγ, IL-6, soluble IL-6R, and GM-CSF), as do bystander immune cells, such as monocytes and/or macrophages (which secrete IL-1Ra, IL-10, IL-6, IL-8, CXCL10 (IP-10), CXCL9 (MIG), IFNα, CCL3 (MIP-1α), CCL4 (MIP-1β), and soluble IL-6R), dendritic cells, and others.

CRS can affect any organ system in the body, including cardiovascular, respiratory, integumentary, gastrointestinal, hepatic, renal, hematological, and nervous systems. Patients at high risk of severe CRS include, but are not limited to, those with bulky disease, co-morbidities, and those who develop early onset CRS within three days of cell infusion. High serum levels of cytokines such as IL-6, soluble gp130, IFNγ, IL-15, IL-8, sIL2Ra, IL8, IP10, MCP1, MIG, GM-CSF, TNFα, MIP1β and/or IL-10 either before or one day after CAR-T cell infusion are associated with subsequent development of severe CRS. In general, there is a balance between the proinflammatory and anti-inflammatory mechanisms, which determines the intensity of the inflammatory response and maintains the immune homeostasis. The proinflammatory and anti-inflammatory cytokines are regulated by complex regulatory networks involving lymphocytes (B cells, T cells, and/or natural killer cells), myeloid cells (macrophages, dendritic cells, and monocytes) and endothelial cells. Moreover, each cytokine also can exert inductive and inhibitive effects on other cytokines, making a cytokine matrix that is responsible for balance regulation.

CRS and related disorders are not restricted to CAR-T cell therapy, and are also associated with therapeutic monoclonal antibodies such as anti-CD3 (OKT3), anti-CD20 (rituximab), anti-CD28 (TGN1412), anti-CD52 (alemtuzumab), CD3/CD19 bispecific antibody (blinatumomab), and anti-PD-1 (nivolumab). Immunodepletion agents such as these may also lead to neurotoxicity and/or neurological events in patients. Without being bound by theory, while CRS and related disorders and neurotoxicity may be associated, the CRS does not cause the neurotoxicity sometimes observed in patients, with the neurotoxicity arising at different times from the development of CRS and related disorders.

The onset of CRS toxicity usually occurs within the first week after immunotherapy (e.g. CAR-T cell therapy or monoclonal antibody) administration, and typically peaks within 1 to 2 weeks of administration. CRS tends to occur earlier in patients treated with certain types of CAR-Ts. For example, patients treated with anti-CD-19-CD28-CD3 CARS may develop CRS earlier than those treated with anti-CD19-4-1BB-CD3 CARs.

Patients should be monitored after therapy (see Table 1). Monitoring should include assessment of vital signs at least every 4 hours, and daily review of organ systems, physical exam, complete blood count with differential, complete metabolic profile, coagulation profiles, and measurement of serum CRP and ferritin levels. Laboratory tests, including blood counts and chemistry panel may need to be performed more than once daily, especially for patients at high risk of severe CRS and/or CRES (i.e. CAR-T associated neurotoxicity/ICANS), or those patients with a high tumor burden who are at risk of tumor lysis. For the latter group, precautions to avoid tumor lysis should be used. Owing to a high risk of arrhythmias, cardiac monitoring by telemetry is advised from the time of CAR-T cell or antibody treatment until resolution of any emergent CRS symptoms. Additional investigations, such as chest radiography, electrocardiography, echocardiography, electroencephalography (EEG), and imaging studies may be performed. Daily fluid balance and bodyweight should be strictly monitored, and maintenance of intravenous hydration is recommended for all patients with, or at risk of developing, CRS.

TABLE 1

| Box 1 Supportive-care considerations for CAR-T-cell therapy |
|---|
| Before and during CAR-T-cell infusion |
| Baseline brain MRI to rule out any central nervous system (CNS) disease<br>Central venous access, preferably with double or triple lumen catheter, for intravenous fluid and other infusions in case of toxicities<br>Cardiac monitoring by telemetry starting on the day of CAR-T-cell infusion and continued until cytokine-release syndrome (CRS) resolves in order to detect arrhythmias<br>Tumour lysis precautions for patients with bulky tumours, as per standard institutional guidelines<br>Seizure prophylaxis with levetiracetam at 750 mg orally every 12 h for 30 days, starting on the day of infusion for CAR-T-cell therapies known to cause CAR-T-cell-related encephalopathy syndrome (CRES (i.e. CAR-T associated neurotoxicity/ICANS))<br>Hospitalization recommended for at least 7 days after CAR-T-cell therapy<br>Patient monitoring after CAR-T-cell infusion |
| Assess vital signs every 4 h, close monitoring of oral and intravenous fluid input and urine output, and daily measurement of bodyweight<br>Daily review of patient history and physical examination<br>Daily blood counts, complete metabolic profiling, and coagulation profiling<br>C-reactive protein and ferritin levels measured daily, starting on the day of infusion<br>Assessment and grading of CRS should be done at least twice daily, and whenever the patient's status changes<br>Assessment and grading of CRES using the CAR-T-cell-therapy-associated toxicity 10-point neurological assessment (CARTOX-10; TABLE 4) should be done at least every 8 h<br>Maintenance intravenous fluids with normal saline to ensure adequate hydration |

TABLE 1-continued

Box 1 Supportive-care considerations for CAR-T-cell therapy

Notifications and contingency orders

The physician should be notified on detection of any of the following: systolic blood pressure (SBP) >140 mmHg or <90 mmHg; heart rate >120 bpm or <60 bpm, or arrhythmia; respiratory rate >25 breaths per min or <12 breaths per min; arterial oxygen saturation <92% on room air; urine output <1,500 ml per day; upward trend in blood creatinine levels or the results of liver function tests; tremors or jerky movements in extremities; change in mental status (alertness, orientation, speech, ability to write a sentence, or CARTOX-10 score)
For patients with a temperature ≥38.3° C., order blood cultures (central and peripheral), urinalysis and urine cultures, portable chest radiography, and notify physician
For patients with neutropenia and fever, start empiric broad-spectrum antibiotics
Corticosteroids should not be administered unless approved by physician
If patient develops CRES, withhold oral intake of food, fluids, and medicine, and notify physician
Pro re nata (as needed) medications, acetaminophen (first choice) or ibuprofen (second choice, if not contraindicated), and cooling blanket for fever ≥38.3° C.; normal saline 500-1,000 ml bolus for SBP <90 mmHg, with one repeat if SBP remains <90 mmHg after first bolus
Anti-IL-6 therapy with tocilizumab or siltuximab to be initiated only on physician order
CAR, chimeric antigen receptor.

IL-6 and IL-6R Antagonists

Studies have observed a strong correlation of peak CAR-T cell levels and serum IL-6 levels with the severity of CRS. IL-6 can signal by 'cis-signaling', via direct binding to membrane-bound IL-6R and gp130 complexes, or by 'trans-signaling', whereby IL-6 binds to soluble IL-6R and the resultant ligand-receptor complex interacts with membrane-bound gp130; both routes lead to activation of JAK/STAT pathway signaling. The expression of membrane-bound IL-6R is restricted to hematopoietic cells, such as macrophages, neutrophils, and T cells, as well as hepatocytes, whereas membrane-bound gp130 is expressed abundantly on all cell types. Thus, cis-signaling, which is activated at low levels of IL-6, affects only a few cell types and mediates anti-inflammatory effects. By contrast, trans-signaling predominates at higher levels of IL-6 (as observed in patients with CRS), can affect most cell types, and mediates proinflammatory effects. Hence, tocilizumab or the chimeric anti-IL-6 mAb siltuximab have become the drugs of choice for the management of moderate-to-severe CRS. Also together with the approval of tisagenlecleucel, the FDA also approved tocilizumab for the treatment of CRS occurring after CAR-T-cell therapy. Siltuximab has been used for the management of CRS and induces rapid reversal of CRS symptoms in most patients. Use of these agents does not seem to affect the efficacy of CAR-T-cell therapy, in terms of response rates or the durability of responses.

Without being bound by theory, IL-6 binds to IL-6R with an affinity (Kd) of around 1 nM, whereas tocilizumab binds to IL-6R with a Kd of 2.54 nM; therefore, IL-6 might compete with tocilizumab for binding to IL-6R. By contrast, siltuximab inhibits IL-6 with a Kd of ~1 µM and, thus, IL-6R is unlikely to compete favorably with siltuximab for IL-6 binding. Siltuximab might be a more-effective treatment than tocilizumab for controlling CRS. In addition, serum IL-6 levels have been shown to increase after administration of tocilizumab, presumably by preventing the IL-6R-mediated uptake of IL-6 into peripheral tissues; thus, a theoretical concern is that this effect might increase passive diffusion of IL-6 into the central nervous system (CNS) and thereby increase the risk of neurotoxicity. This scenario is unlikely to occur with siltuximab because it binds directly to IL-6. Prospective clinical studies are needed to directly compare the effectiveness of tocilizumab and siltuximab (or both in combination) in the treatment of CRS.

Corticosteroids Usage

Corticosteroids also suppress inflammatory responses and are effective in the management of CRS, CRES (i.e. CAR-T associated neurotoxicity/ICANS), and HLH/MAS associated with immunotherapies. However, because corticosteroids suppress T-cell function and/or induce T-cell apoptosis, use of these drugs should be avoided for other indications (such as premedication for blood transfusions) after adoptive T-cell therapy. Of note, data from studies in allogeneic stem-cell transplant recipients have demonstrated that cytomegalovirus-specific T cells can persist despite corticosteroid therapy, but have impaired cytokine production. In the setting of cell based immunotherapy, these findings suggest that corticosteroids will impair the function, if not the persistence, of the infused tumor-directed T cells. Given these concerns, the use of corticosteroids is generally considered only when the toxicities of CAR-T-cell therapy are refractory to anti-IL-6 therapy.

Management of CRS

CRS may be managed in accordance with the grade of this toxicity (See Table 2). Further, updated CRS grading may be found in Lee et al. (2018) Biol. Blood Marrow Transplant. December 25. pii: S1083-8791(18)31691-4, the contents of which are incorporated herein by reference in their entirety.

TABLE 2

Grading of cytokine-release syndrome (CRS)

| Symptom or sign of CRS | CRS grade 1* | CRS grade 2* | CRS grade 3* | CRS grade 4* |
|---|---|---|---|---|
| Vital signs | | | | |
| Temperature ≥38% C. (fever) | Yes | Any | Any | Any |
| Systolic blood pressure <90 mmHg (hypotension) | No | Responds to IV fluids of low-dose vasopressors | | |
| Needing oxygen for SaO$_2$ >90% (hypoxia) | No | FiO$_2$ <40% | | |
| Organ toxicities | | | | |
| Cardiac: tachycardia, arrhythmias, heart block, low ejection fraction | Grade 1 | Grade 2 | Grade 3 or grade 4 transaminitis | Grade 4 except grade 4 transaminitis |
| Respiratory: tachyupnoea, pleural effusion, pulmonary oedema | | | | |
| GI: nausea, vomiting, diarrhea | | | | |
| Hepatic: increased serum ALT, AST, or bilirubin levels | | | | |
| Renal: acute kidney injury (increased serum creatinine levels), decreased urine output | | | | |
| Dermatological rash (less common) | | | | |
| Coagulopathy: disseminated intravascular coagulation (less common) | | | | |

Grade 1 CRS is primarily managed with supportive care; the use of maintenance intravenous fluids is recommended to keep patients well-hydrated, with special attention to fluid balance in order to avoid pulmonary vascular congestion. Additionally, anti-IL-6 therapy with tocilizumab or siltuximab is recommended for hypotension that is refractory to fluid boluses (with response rates >95% per Neelapu et al), and can be repeated if needed. If hypotension persists, low-dose vasopressors should be initiated and titrated to achieve a systolic blood pressure of >90 mmHg, and transfer of the patient to an intensive-care unit (ICU) should be considered. Bedside echocardiography to determine ejection fraction is recommended for patients with persistent or repeated episodes of hypotension, because left ventricular dysfunction can occur in patients with CRS. Moreover, non-invasive monitoring of hemodynamic parameters, such as inferior vena cava filling pressures, passive leg raise, pulse pressure, and stroke volume variation, can help guide the management of hypotension, in terms of the need for intravenous fluids, vasopressors, or inotropic agents. Hypoxia associated with either noncardiogenic pulmonary edema or pleural effusions should be managed with supplemental oxygen and diuresis, or thoracentesis, if indicated. Anti-IL-6 therapy is recommended, and can be repeated as needed, for patients with persistent hypoxia at a fraction of inspired oxygen (FiO2)<40% and other grade 2 organ toxicities. Other organ toxicities should be managed symptomatically according to standard guidelines.

For patients at high risk of severe CRS (grade 3 or 4), or those with persistent grade 2 CRS despite anti-IL-6 therapy, the use of corticosteroids can be considered. Patients with grade 3 or 4 CRS should be treated in the ICU to enable continuous monitoring, management of life-threatening arrhythmias, hemodynamic shock, non-invasive positive pressure ventilation, mechanical ventilation, and/or dialysis. Both anti-IL-6 therapy and corticosteroids should be used for the management of grades 3 and 4 CRS, and the associated organ toxicities. Corticosteroid tapering should be individualized depending on the patient's response and any adverse effects, but is generally recommended to be as rapid as possible. Serum CRP levels are a useful marker to monitor in patients undergoing cellular immunotherapy because IL-6 induces the production of CRP by hepatocytes. Thus, an increase in serum CRP level is typically detected after the onset of CRS, and correlates with increased levels of IL-6. Moreover, the return of CRP levels to baseline indicates that the CRS phase of CAR-T-cell therapy has ended. Of note, the correlation between CRP levels and CRS is variable, and is not observed in all patients. The correlation between serum ferritin levels and CRS is even less consistent. Nevertheless, monitoring ferritin levels can be useful for diagnosis of CAR-T-cell-related HLH/MAS. Grading and management of CRS may be managed according to Table 3 below or updated CRS grading may be found in Lee et al. (2018) Biol. Blood Marrow Transplant. December 25. pii: S1083-8791(18)31691-4, the contents of which are incorporated herein by reference in their entirety.

TABLE 3

Recommendations for the management of cytokine-release syndrome (CRS)

| CRS grade | Symptom or sign | Management |
|---|---|---|
| Grade 1 | Fever or organ toxicity | Acetaminophen and hypothermia blanket for the treatment of fever Ibuprofen can be used as second treatment option for fever, if not contraindicated |

TABLE 3-continued

Recommendations for the management of cytokine-release syndrome (CRS)

| CRS grade | Symptom or sign | Management |
|---|---|---|
| Grade 2 | | Assess for infection using blood and urine cultures, and chest radiography<br>Empiric broad-spectrum antibiotics and filgrastim if neutropenic<br>Maintenance intravenous (IV) fluids for hydration<br>Symptomatic management of constitutional symptoms and organ toxicities<br>Consider tocilizumeb 8 mg/kg* IV or siltuximeb 11 mg/kg IV for persistent (lasting >3 days) and refractory fever |
| | Hypotension | IV fluid bolus of 500-1,000 ml of normal saline<br>Can give a second IV fluid bolus if systolic blood pressure (SBP) remains <90 mmHg<br>Tocilizumab 8 mg/kg* IV or siltuximab 11 mg/kg IV for the treatment of hypotension that is refractory to fluid<br>boluses: tocilizumab can be repeated after 6 h if needed<br>If hypotension persists after two fluid boluses and anti-IL-6 therapy. Start vasopressors, consider transfer to intensive-care unit (ICU), obtain echocardiogram, and initiate other methods of haemodynamic monitoring<br>Inpatients at high-risk† or if hypotension persists after 1-2 doses of anti-IL6 therapy, dexamethasone can be used at 10 mg IV every 6 h<br>Manage fever and constitutional symptoms as in grade 1 |
| | Hypoxia | Supplemental oxygen<br>Tocilizumab or siltuiximab ± corticosteroids and supportive care. as recommended for the management of hypotension |
| | Organ toxicity | Symptomatic management of organ toxicities, as per standard guidelines<br>Tocilizumab or siltuximab ± corticosteroids and supportive care, as indicated for hypotension |
| Grade 3 | Hypotension | IV fluid boluses as needed. as recommended for the treatment of grade 2 CRS<br>Tocilizumab and siltuximab as recommended for grade 2 CRS, if not administered previously<br>Vasopressors as needed<br>Transfer to ICU, obtain echocardiogram. and perform haemodynamic monitoring as in the management of grade 2 CRS<br>Dexamethasone 10 mg IV every 6 h: if refractory, increase to 20 mg IV every 6 h<br>Manage fever and constitutional symptoms as indicated for grade 1 CRS |
| | Hypoxia | Supplemental oxygen including high-flow oxygen delivery and non-invasive positive pressure ventilation<br>Tocilizumab or siltuximab plus corticosteroids and supportive care, as described above |
| | Organ toxicity | Symptomatic management of organ toxicities as per standard guidelines<br>Tocilizumabor siltuiximab plus corticosteroids and supportive care, as described above |
| Grade 4 | Hypotension | IV fluids, anti-IL-6 therapy, vasopressors, and haemodynamic monitoring as defined for the management of Grade 3 CRS<br>Methylprednisolone 1 g/day IV<br>Manage fever and constitutional symptoms as in grade 1 CRS |
| | Hypoxia | Mechanical ventilation<br>Tocilizumab or siltuximab plus corticosteroids and supportive care, as described above |
| | Organ toxicity | Symptomatic management of organ toxicities as per standard guidelines<br>Tocilizumab or siltuximab plus corticosteroids and supportive care, as described above |

All medication doses indicated are for adults.
*Maximum amount of tocilizumab per dose is 800 mg.
†High-risk patients include those with bulky disease, those with comorbidities, and those who develop early onset CRS within 3 days of CAR-T-cell infusion.

Symptoms and Signs of CRES (or CAR-T Neurotoxicity or ICANS)

CRES (i.e. CAR-T associated neurotoxicity/ICANS) typically manifests as a toxic encephalopathy, with the earliest signs being diminished attention, language disturbance, and impaired handwriting; other symptoms and signs include confusion, disorientation, agitation, aphasia, somnolence, and tremors. In severe cases of CRES (grade >2), seizures, motor weakness, incontinence, mental obtundation, increased intracranial pressure, papilledema, and cerebral edema can also occur. The manifestation of CRES can be biphasic; the first phase occurs concurrently with high fever and other CRS symptoms, typically within the first 5 days after cellular immunotherapy, and the second phase occurs after the fever and other CRS symptoms subside, often beyond 5 days after cell infusion. Notably, delayed neurotoxicity with seizures or episodes of confusion occurred during the third or fourth week after CAR-T-cell therapy in approximately 10% of patients. Anti-IL-6 therapy can reverse CRES during the first phase, but is generally not effective in the second phase, when corticosteroids are the preferred treatment. The differential benefit of anti-IL-6 therapy between the two phases could potentially reflect greater permeability of the blood-brain barrier (BBB) during CRS than at the later post-CRS phase, enabling increased diffusion of the mAb therapeutics into the brain. CRES typically lasts for 2-4 days, but can vary in duration from a few hours to weeks. In general, CRES occurring concurrently with CRS tends to be of shorter duration and lower grade (grade 1-2) than CRES occurring post-CRS, which is more commonly grade ≥3 and protracted. Moreover, the severity of CRES can fluctuate rapidly, thus, necessitating close patient monitoring. CRES is often disturbing to the patient, their families, and the medical staff, but is generally reversible; although, rare fatal cases have occurred.

Pathophysiology of CRES (or CAR-T Neurotoxicity or ICANS)

CRES may, without being bound by theory, be caused by passive diffusion of cytokines such as IL-6 and IL-15 into the brain or trafficking of T cells into the CNS. Indeed, in one study, CAR-T-cell numbers were found to be significantly higher in cerebrospinal fluid (CSF) from patients with neurotoxicity as compared to those without neurotoxicity (P=0.0039).

The numbers of circulating CAR-T cells also tend to be higher in patients who develop neurotoxicity than in those who do not. Of note, protein levels in the CSF are usually elevated in patients with CRES, compared with baseline measurements, suggesting disruption of the blood-brain barrier (BBB). Other organ dysfunction (hepatic and renal), as well as hypoxaemia, and infection, might also contribute to the encephalopathy.

The incidence of non-convulsive status epilepticus (NCSE) in patients treated with CAR-T-cell therapy is approximately 10%, with some patients (<5%) developing NCSE after convulsive status epilepticus. Seizure prophylaxis with levetiracetam 750 mg orally or intravenously every 12 h is recommended for 30 days, starting on the day of infusion for patients undergoing CAR-T-cell therapies that are known to cause CRES. Levetiracetam is the preferred agent for seizure prophylaxis because it has a better drug-drug interaction profile and lower risk of cardiotoxicity compared with those of other antiepileptic agents, and can be administered safely to patients with hepatic dysfunction; although, dose adjustments might be needed for those with renal dysfunction. Furthermore, cytokine levels are not affected by levetiracetam treatment. Of note, not all CAR or TCR-engineered T-cell products have been associated with CRES. Thus, for patients undergoing treatment with new agents that have an unknown risk of CRES, seizure prophylaxis can be omitted until data from initial clinical trials have been analyzed. MRI and CT scans of the brain are usually negative for any anatomical pathology that would account for the neurotoxicity symptoms observed in patients treated with CAR-T-cell therapy, although rare cases of reversible T2/fluid attenuated inversion recovery (FLAIR) MRI hyperintensity involving the thalami, dorsal pons, and medulla, and cerebral edema have been reported. Of note, life-threatening cerebral edema, although very rare in patients treated with cellular immunotherapy, tends to have a very rapid course with ensuing brain death within 24 h. Notably, in March 2017, five deaths attributed to cerebral edema were reported following treatment of the patients with one anti-CD19 CAR-T-cell product (JCAR015) as part of a multicenter clinical trial.

Grading of CRES (or CAR-T Neurotoxicity or ICANS)

Similar to other organ toxicities, CRES (i.e. CAR-T associated neurotoxicity/ICANS) has been graded according to the CTCAE v4.03, in terms of level of consciousness, orientation, ability to perform activities of daily living (in the context of encephalopathy), speech, tremors, seizures, incontinence, and motor weakness. (see Table 4). The CTCAE grading system does not, however, adequately quantify the acute neurological deficits that seem to be unique toxicities of CAR-T-cell therapies. Thus, a new grading system for CRES has been developed, together with the CARTOX 10-point neurological assessment (CARTOX-10) tool. This tool is based on experiences in the observation and treatment of more than 50 adult patients with grade 1-5 neurotoxicity from CAR-T-cell therapy at MDACC, approximately 50% of whom developed grade ≥3 neurological adverse events. The CARTOX-10 incorporates some of the key elements of the 30-point MMSE, encompassing the predominant alterations in concentration, speech, and writing ability that are associated with CRES, to enable evaluation of the acute neurotoxic events observed in patients treated with CAR T cells using a 10-point scale. In the CARTOX-10, one point is assigned for each of the following tasks that is performed correctly: orientation to year, month, city, hospital, and President/Prime Minister of country of residence (total of 5 points); naming three objects (maximum of 3 points); writing a standard sentence (1 point); counting backwards from 100 in tens (1 point). Normal cognitive function is defined by an overall score of 10. Grading of CRES (i.e. CAR-T associated neurotoxicity/ICANS) may be found in Lee et al. (2018) Biol. Blood Marrow Transplant. December 25. pii: S1083-8791(18) 31691-4, the contents of which are incorporated herein by reference in their entirety. In comparison with the MMSE, which is used to screen patients for dementia (not delirium), the CARTOX-10 is simple to use, and can be performed rapidly and repeatedly several times a day by all health-care providers, including nurses and physicians. The tasks used in the CARTOX-10 can be simplified depending on the education level of the patient, but need to be documented, together with a baseline score, before CAR-T-cell infusion, to ensure that follow-up assessments are reliable and consistent; however, this tool is primarily designed for the assessment of adult patients, and alternative tools need to be developed to assess children. It is recommended that the 10-point neurological assessment be performed every 8 h while the patient is hospitalized after CAR-T-cell therapy. Any change from a normal score should prompt thorough investigation as described in the following section of this manuscript. Patients who are aphasic (CARTOX-10 score of 0), but awake/arousable and without other neurological symptoms or signs (such as motor weakness, seizures and papilledema), are considered to have grade 3 CRES. In addition to the CARTOX-10, parameters including papilledema, CSF opening pressure, and imaging assessment are incorporated into CRES grading system, in order to detect signs of raised intracranial pressure and cerebral edema. In contrast with the CTCAE v4.03, seizures are upgraded to a grade 3 or 4 adverse event in the proposed CRES grading system. Thus, the advantages of this grading system over the CTCAE include greater objectivity and ease of application.

Management of CRES.

Similar to CRS, the management of CRES (i.e. CAR-T associated neurotoxicity/ICANS) is based on the toxicity grade as outlined in Table 4 or Lee et al. (2018) Biol. Blood Marrow Transplant. December 25. pii: S1083-8791(18) 31691-4, the contents of which are incorporated herein by reference in their entirety. Grade 1 CRES is primarily managed with supportive care. The head of the patient's bed should be elevated by at least 30 degrees to minimize aspiration risks and to improve cerebral venous flow. A thorough neurological evaluation, including EEG and funduscopic examination to rule out papilledema, of all patients with CRES, regardless of grade should be performed. Neuroimaging and CSF opening pressure, if available, are much better surrogates of increased intracranial pressure and possible cerebral edema than papilledema; however, lumbar puncture might also be infeasible when patients are restless or have coagulopathy. In patients with an ommaya reservoir, opening pressure can be measured in the supine position with the base of the manometer placed at heart level. Combinations of these techniques should be considered to diagnose increased intracranial pressure and cerebral edema.

In particular, repeated neuroimaging, is recommended to detect early signs of cerebral edema in patients with grade 3 or 4 CRES, and in patients with rapid changes in the CRES grade (increase in grade by two levels, for example, grade 1 CRES worsening to grade 3). The clinical status of the patient often dictates the choice of neuroimaging modality: MRI of the brain is preferred, but cannot be performed for unstable or agitated patients, whereas CT can be. The development of cerebral edema in patients treated with CAR T cells is associated with other acute and clinically significant neurological changes, such as a low CARTOX-10 score and/or seizures. Anti-IL-6 therapy is recommended for patients with grade >1 CRES with concurrent CRS; if not associated with CRS, corticosteroids are the preferred treatment for grade ≥2 CRES, and can be tapered after improvement of CRES to grade 1. The optimal duration of corticosteroid therapy remains unknown, although in our experience, short courses of steroids have been associated with resolution of neurological toxicities without impaired antitumor responses. Patients should be monitored closely for recurrence of neurotoxicity symptoms during corticosteroid tapering. Monitoring is required for all patients with grade 4 CRES because they might need mechanical ventilation for airway protection. Non-convulsive and convulsive status epilepticus in these patients should be managed with benzodiazepines and additional antiepileptics (preferably with levetiracetam), as needed. After levetiracetam, phenobarbital is the preferred second antiepileptic for the management of CRES-related seizures: phenytoin and lacosamide are associated with higher risks of cardiovascular adverse effects, therefore, their use in patients with concurrent CRS should be excluded to avoid arrhythmias and hypotension. Grade 3 CRES with raised intracranial pressure should be managed promptly with corticosteroids and acetazolamide; patients who develop grade 4 CRES with cerebral edema should receive high-dose corticosteroids, hyperventilation, and hyperosmolar therapy.

vation could identify the CAR-T patients who face the highest risk of severe side effects.

Hay et al. analyzed the kinetics and biomarkers of severe CRS after anti-CD19-CART therapy. In 133 patients analyzed, CRS developed in 70% of patient (Grade 1, 26%; grade 2, 32%; grade 3, 4.5%; grade 4, 3.8% and grade 5, 3.8%). A large panel of serum biomarkers was analyzed during this period of treatment with CAR-T, and it was found that severe CRS was associated with elevated levels of angiopoietin-2 and von Willebrand factor, which are released from Weibel-Palade bodies on endothelial activation. This is in accordance with the clinical characterization of severe CRS with hemodynamic instability, capillary leak and consumptive coagulopathy. The levels of these biomarkers are elevated not only during CRS but also before lymphodepletion in patients who subsequently developed CRS.

Hay et al. also performed analysis focusing on CRES. In this study 7 (5%) developed grade 4/5 neurotoxicity, and 4 died with neurotoxicity including multifocal brainstem hemorrhage with edema, acute cerebral edema and cortical laminar necrosis. With the exception of these fatal cases and one whose grade 1 neurotoxicity persisted over 2 months, neurotoxicity completely resolved in all patients by day 28. Severe CRES is associated with DIC, capillary leak and increased blood-brain barrier permeability. Similar to the analysis of CRS, ANG2 and vWF levels were higher in patients who developed severe neurotoxicity (Grade 4/5) than in those with no or mild toxicity (Grade 0-3). In addition, they evaluated cytokine concentrations in paired blood and CSF samples, obtained before lymphodepletion and during acute neurotoxicity. During acute neurotoxicity concentrations of IFNg, TNFα, IL6 and TNFRp55 had increased markedly and were comparable between serum and CSF, suggesting that the BBB did not prevent high plasma cytokine concentrations from transitioning into CSF or that there was local cytokine production in the CSF.

TABLE 4

Grading of CAR-T-cell-related encephalopathy syndrome (CRES)

| Symptom or sign | Grade 1 | Grade 2 | Grade 3 | Grade 4 |
|---|---|---|---|---|
| Neurological assessment score (by CARTOX-10*) | 7-9 (mild impairment) | 3-6 (moderate impairment) | 0-2 (severe impairment) | Patient in critical condition, and/or obtunded and cannot perform assessment of tasks |
| Raised intracranial pressure | N/A | N/A | Stage 1-2 papilloedema† or CSF opening pressure <20 mmHg | Stage 3-5 papilloedema† or CSF opening pressure ≥20 mmHg, or cerebral oedema |
| Seizures or motor weakness | N/A | N/A | Partial seizure, or non-convulsive seizures on EEG with response to benzodiazepine | Generalized seizures, or convulsive or non-convulsive status epilepticus, or new motor weakness |

CAR, chimeric antigen receptor; CARTOX-10, CAR-T-cell-therapy-associated toxicity 10-point neurological assessment CSF, cerebrospinal fluid;
EEG, electroencephalogram; NA, not applicable.
*In the CARTOX-10, one point is assigned for each of the following tasks that is performed correctly (normal cognitive function is defined by an overall score of 10); orientation to year, month, city, hospital, and President/Prime Minister of country of residence (total of 5 points); name three objects - for example, point to clock, pen, button (maximum of 3 points); write a standard sentence, for example, "our national bird is the bald eagle" (1 point); count backwards from 100 in tens (1 point).
†Papilloedema grading is performed according to the modified Frisén scale.

Evidence Suggesting Endothelial Activation and Damage in CRS and CRES

One characteristic common in patients who suffered severe cytokine release or neurotoxicity was that the endothelial cells in the linings of the patient's blood vessels became hyperactivated, the discovery of which lead researchers to test whether biomarkers for endothelial acti- Upon autopsy of 2 patients who developed fatal CRS and CRES, multifocal microhemorrhages and patchy parenchymal necrosis in the pons, medulla and spinal cord were observed. Intravascular vWF binding and CD61+ platelet microthrombi were observed, consistent with endothelial activation. Severe CRES is associated with DIC, capillary leak and increased blood-brain barrier permeability. Similar to the analysis of CRS, ANG2 and vWF levels were higher in patients who developed severe neurotoxicity (Grade 4/5) than in those with no or mild toxicity (Grade 0-3). In addition, they evaluated cytokine concentrations in paired blood and CSF samples, obtained before lymphodepletion and during acute neurotoxicity. During acute neurotoxicity concentrations of IFNg, TNFα, IL6 and TNFRp55 had increased markedly and were comparable between serum and CSF, suggesting that the BBB did not prevent high plasma cytokine concentrations from transitioning into CSF or that there was local cytokine production in the CSF.

Neurotoxicity

CRS or CRES (i.e. CAR-T associated neurotoxicity/ICANS—also referred to herein as neurological events) may be observed in patients undergoing immunodepletion therapies such as CAR-T, monoclonal antibodies, and/or bispecific antibodies. The median onset of neurological events occurs 4-5 days after CAR-T cell infusion, but can also be concurrent with CRS, follow resolution of CRS, or occur alone. (Wang and Han (2018)).

Administration of immunodepletion agents can cause an adverse effect on the structure or function of the central nervous system and/or the peripheral nervous system. In some embodiments, the therapeutic agent causes permanent damage to the nervous tissue. In some embodiments, the therapeutic agent causes reversible damage to the nervous tissue. In some embodiments, the damage to the nervous system is the disruption or killing of neurons. In some embodiments, the symptoms of neurotoxicity appear immediately after exposure to a therapeutic agent. In some embodiments, the symptoms of neurotoxicity are delayed after exposure to a therapeutic agent. Symptoms of neurotoxicity include, but are not limited to, limb weakness or numbness, loss of memory, vision impairment, cognition impairment, uncontrollable obsessive and/or compulsive behaviors, delusions, headache, cognitive and behavioral problems, and sexual dysfunction.

In some embodiments, administration of a lymphodepletion agent (e.g. CAR-T, antibody, or bispecific antibody) produces a neurological event in a subject. In some embodiments, the neurological event is a Grade 1, Grade 2, Grade 3, Grade 4, or Grade 5 event, or a combination thereof.

In some embodiments, the subject develops only a neurological event after administration of a lymphodepletion agent. In some embodiments, the subject develops only CRES (or CAR-T neurotoxicity or ICANS) after administration of a lymphodepletion agent. In some embodiments, the subject develops CRES (or CAR-T neurotoxicity or ICANS) and CRS after administration of a lymphodepletion agent. In some embodiments, the subject develops a neurological event that is not CAR-T neurotoxicity, ICANS or CRES after administration of a lymphodepletion agent. In some embodiments, the subject develops both a neurological event (that is not CAR-T neurotoxity, ICANS or CRES) and CRS and/or CRES. In some embodiments, the neurological event that is not CAR-T neurotoxicity, ICANS or CRES occurs at the same time as CRS and/or CRES. In some embodiments, the neurological event that is not CAR-T neurotoxicity, ICANS or CRES occurs separately from CRS and/or CRES. In some embodiments, the neurological event is aphasia, encephalopathy, delirium, seizure and seizure-like activity, tremor/myoclonus, hallucinations, diffuse cerebral edema, dizziness, confused state, headache, fatigue, speech disorder, somnolence, paresthesia, ataxia, lethargy, dysathria, hypoesthesia, amnesia, bradyphrenia, delirium, hyperreflexia, nystagmus, abnormal reflexes, restless leg syndrome, and/or disorientation.

In some embodiments, the development of neurotoxicity and/or neurological events is determined by measuring one or more serum biomarkers. In some embodiments, the biomarkers are cellular debris, DNA, and/or proteins released by the destruction of nerve cells. In some embodiments, the biomarkers are stress proteins. In some embodiments, the biomarkers are selected from a group comprising, but not limited to, MAO and ChE enzyme activity, D2 receptor, mACh receptor, Hsp70, autoantibodies, c-fos expression, ornithine decarboxylase gene expression, cerebrospinal fluid markers, and/or plasma components (e.g. myelin basic protein, anti-NF, anti-myelin antibody, anti-GFAP antibody, anti-nerve growth factor antibody), IFNg, TNFRp55, Endothelin-1, soluble Vascular Cell Adhesion Molecule (VCAM), Intra-Cellular Adhesion Molecule (ICAM), E-selectin, soluble Thrombomodulin, Von Willebrand factor (vWF), DAMP (damage-associated molecular patterns), and PAMP (pathogen-associated molecular patterns) or a combination thereof. In some embodiments, the marker is a change in behavior or physiological measurement (e.g. electroencephalogram) as compared to an unaffected subject or the same subject before administration of a CAR-T, monoclonal antibody, or bispecific antibody.

In some embodiments, defibrotide is administered to a patient experiencing neurotoxicity and/or a neurological event. In some embodiments, defibrotide is administered to a patient at risk of experiencing neurotoxicity and/or a neurological event. In some embodiments, risk factors include age, with patients older than 65 years of age having a greater risk of developing neurological events, prior neurologic disorders, patients having received more than 2 prior salvage therapies, and non-white patients. In some embodiments, patients who developed CRS and/or CRES are at greater risk of developing neurotoxicity and/or neurological events. In some embodiments, there is no correlation between the development of CRS and/or CRES and the development of neurotoxicity and/or neurological events Bispecific Antibodies In some aspects, the lymphodepletion agent is a bispecific antibody. These antibodies are designed to bind the target cell (e.g. a cancer cell) and activating receptors on cytotoxic cells such as T-cells or NK cells. Bispecific antibodies may also comprise two different Fabs so that the antibody simultaneously binds to two different types of antigen. In some embodiments, the bispecific antibody is a monoclonal antibody. In some embodiments, the bispecific antibody is an IgG-like bispecific antibody, which contains two Fab arms, each of which binds a different antigen, and one Fc region. In some embodiments, the bispecific antibody is a trifunctional antibody. In some embodiments, the bispecific antibody in a non-IgG-like antibody, which lacks an Fc region. These include, but are not limited to, chemically linked Fabs, bivalent single-chain variable fragments, trivalent single-chain variable fragments, fusion proteins mimicking the variable domains of two antibodies, and bi-specific T-cell engagers (BiTEs).

In some embodiments, the bispecific antibody is an immunotherapeutic. In some embodiments, the bispecific antibody is a cancer immunotherapeutic. In some embodiments, the bispecific antibody binds to an antigen on an immune cell. In some embodiments, the bispecific antibody binds to a T-cell. In some embodiments, the bispecific antibody binds to a tumor antigen. In some embodiments, the bispecific antibody binds to an antigen including, but not limited to, CD33, CD3, CD19, CD47, EpCAM, transferrin, β-secretase (BACE1), Her2/neu, EFFR, CEA, EpHA2, MCSP, and/or CD20).

In some embodiments, the bispecific antibody is selected from the group including, but not limited to, AMV564, Blinatumomab, Emicizumab (Hemlibra), catumaxomab, ertumaxomab, and/or FBTA05.

Defibrotide and its Mechanisms of Action

Defibrotide (CAS number 83712-60-1) is a substance derived from materials of natural origin. Defibrotide, a nucleic acid salt, is a highly complex mixture of random sequences, predominantly single-stranded polydeoxyribonucleotides (predominantly single stranded and approximately 10% double stranded) derived from animal mucosal DNA Defibrotide has pleotropic biologic effect leading to the stabilization of endothelial cells, In particular, defibrotide has protective effects on vascular endothelial cells, particularly those of small vessels and has antithrombotic, anti-inflammatory and antiischemic properties.

Defibrotide has a diverse size range and is known to have a mean molecular weight (MW) between 13 and 20 kDa. Defibrotide can be obtained according to U.S. Pat. Nos. 4,985,552 and 5,223,609 and/or presents the physical/chemical characteristics described in the same U.S. Pat. Nos. 4,985,552 and 5,223,609, each of which is incorporated herein by reference. Synthetic defibrotide, presented as phosphodiester oligonucleotides that mimic the therapeutic action of defibrotide are described in US20110092576 which is incorporated herein by reference in its entirety.

Defibrotide has numerous therapeutic applications, including use as an anti-thrombotic agent (U.S. Pat. No. 3,829,567), treatment of peripheral arteriopathies (U.S. Pat. No. 5,081,109), treatment of acute renal insufficiency (U.S. Pat. No. 4,694,134), treatment of acute myocardial ischaemia (U.S. Pat. No. 4,693,995), protection of endothelial cells (U.S. Pat. No. 5,116,617) among other uses described in U.S. Pat. Nos. 3,770,720, 3,899,481, 4,938,873, 4,985,552, 5,223,609, 5,646,127, 5,646,268, and 6,046,172; all of the preceding patents are incorporated herein by reference in their entireties. More recently, defibrotide has been used for the treatment and prevention of sinusoidal obstruction syndrome/veno-occlusive disease (EU clinical trial EudraCT: 2004-000592-33, US clinical trial 2005-01 (ClinicalTrials-.gov identifier: NCT00358501). Patients are treated with a 6.25 mg/kg dose given as a two hour intravenous infusion every six hours until signs and symptoms of VOD are mitigated. As mentioned above, Defibrotide is currently sold under the name Defitelio® as a single vial for injection (commercially available from Gentium S.r.L., Villa Guardia, Italy; see package insert available at dailymed.nlm.nih.gov/dailymed/search.cfm?labeltype=all&query=defibrotide).

Defitelio® is prepared as an intravenous infusion by a dilution in 5% Dextrose Injection, USP or 0.9% Sodium Chloride Injection, USP. Intravenous preparation is used within 4 hours if stored at room temperature or within 24 hours if stored under refrigeration. It is administered for a total of 8 hours over 4 intravenous infusions.

The sodium salt of defibrotide is commercially sold as Defitelio® (Gentium S.r.L., Villa Guardia, Italy) and is currently approved for the treatment of adult and pediatric patients with hepatic veno-occlusive disease (VOD), also known as sinusoidal obstruction syndrome (SOS), with renal or pulmonary dysfunction following hematopoietic stem-cell transplantation (HSCT). The dosing for prevention, amelioration, or treatment of CRS, CRES, or a related syndrome may be similar to the dosing for prevention or treatment of VOD (e.g. 6.25 mg/kg every 6 hours). Defibrotide is administered to patients by 2-hour intravenous infusions every 6 hours for a minimum of 21 days. The frequency and large volumes of the infusion regimen requires that patients have a second IV line for defibrotide administration to avoid mixing defibrotide with other drugs that must be given IV. The treatment regimen would not be compatible in an outpatient dosing for additional disease indications for which defibrotide may be shown to be therapeutic. Therefore, it would be beneficial to administer defibrotide in a way that is more convenient to the patient to allow dosing in an outpatient setting, allow patients to self-administer at home via a compatible administration device, or reduce dosing duration and liquid volume in a hospital setting. Thus there is a need for new formulations of defibrotide which would permit new and more patient convenient dosing regimens for administration of pharmaceutically effective doses at home.

When defibrotide circulates around endothelial cells, it becomes attached to the external cell membrane and is then internalized by the cells. Furthermore, interaction of defibrotide with the cell membrane is sufficient to guarantee at least two of the several actions attributed to this drug on the endothelium, anti-inflammatory and antioxidant effects. Nonclinical and clinical data suggest that the endothelial protective effect of defibrotide may also be mediated via fibrinolytic, anti-thrombotic, anti-ischemic, and anti-adhesive actions.

Defibrotide was approved in Europe in 2013 and in the United States of America in 2014. Defibrotide is also approved in Europe for the prevention of graft versus host disease. Because of this protective effect of defibrotide in endothelial cells, defibrotide may also have protective effect in other medical conditions involving endothelial activation and damages, including CRS and CRES (or CAR-T neurotoxicity/ICANS).

Defibrotide Administration

Defibrotide may be administered to a patient undergoing, or about to undergo, immunotherapy. In some embodiments, the immunotherapy is immunodepletion chemotherapy. In some embodiments, the immunodepletion chemotherapy is a CAR-T. In some embodiments, the immunotherapy is an anti-cancer antibody or fragment thereof. In some embodiments, the anti-cancer antibody or fragment thereof is a monoclonal antibody. In some embodiments, the immunotherapy is a bi-specific antibody.

The defibrotide may be administered as often and as for long as required. In some embodiments, the defibrotide is administered 1-120 times. In some embodiments, the defibrotide is administered for about one day, about two days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days or more. The defibrotide may be administered daily, weekly, or monthly. In some embodiments, the defibrotide is administered every day for about one week, about two weeks, about three weeks, or about four weeks. In some embodiments, defibrotide administration occurs on consecutive days. In some embodiments, defibrotide administration occurs on discontinuous days. In some embodiments, defibrotide administration continues for three days (with administration of defibrotide on each day occurring immediately prior to lymphodepletion). In some embodiments, defibrotide is not administered on the two days before CAR-T cells are first administered. In some embodiments, defibrotide is administered on the day CAR-T cells are administered (e.g. Study Day 0). In some embodiments, defibrotide is administered until CAR-T Day +7 (e.g. Study Day 13). In some embodiments, a minimum of about 1 to about 5 doses of defibrotide are administered before CAR-T administration. In some embodiments, a minimum of about 1, about 2, about 3, about 4, or about 5 doses are administered before CAR-T administration. In some embodiments, a minimum of two doses of defibrotide are administered before CAR-T administration.

Figure 10:
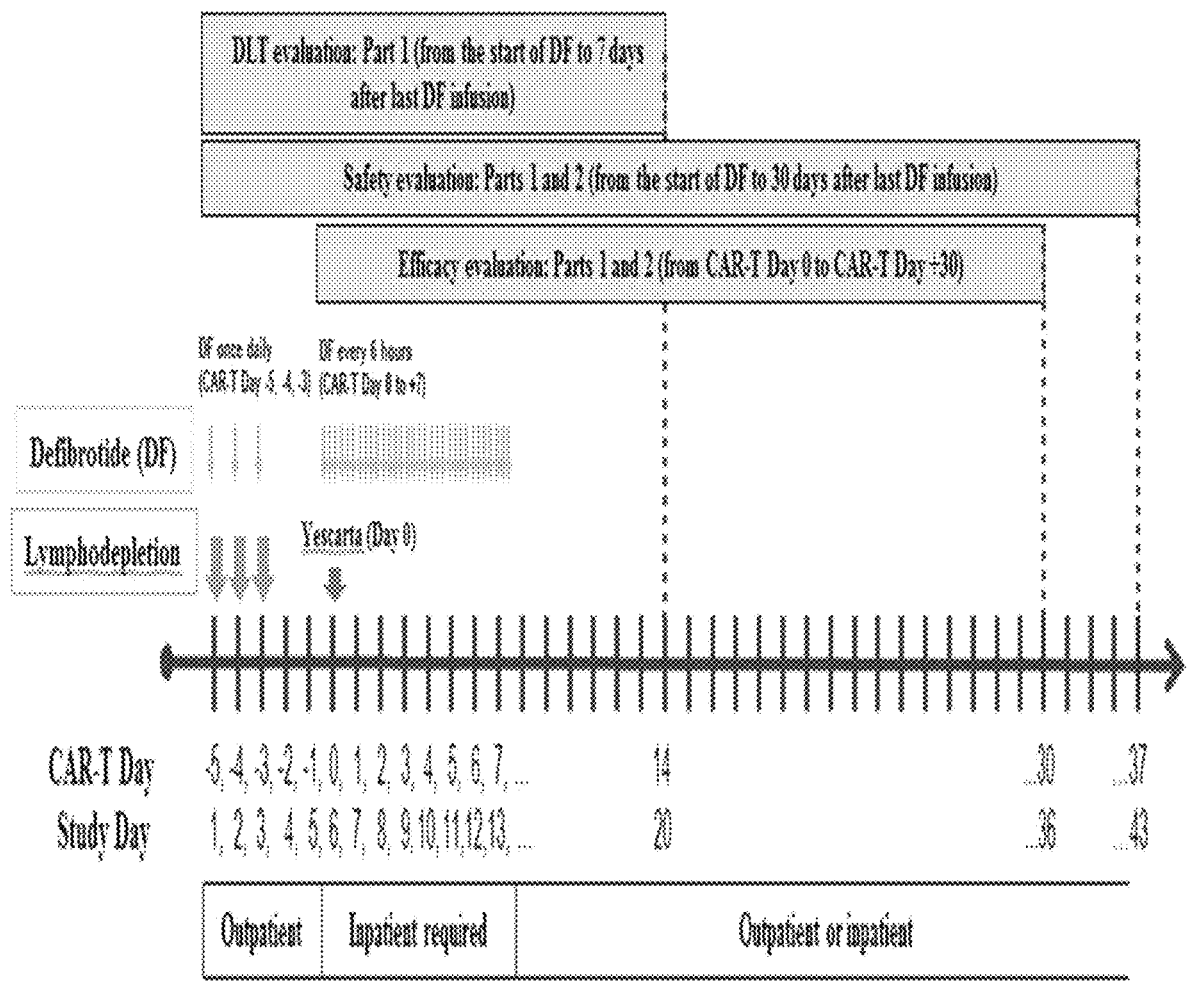
FIG. 10 shows the defibrotide dosing schedule for a Phase 2 study evaluating the safety and efficacy of defibrotide for the prevention of CAR-T-associated neurotoxicity in subjects with relapsed or refractory diffuse large B-cell lymphoma (DLBCL) receiving axicabtagene ciloleucel (Yescarta®).

In some embodiments, the dosing schedule for defibrotide is summarized in FIG. 10.

In some embodiments, the defibrotide is administered multiple times a day. In some embodiments, the defibrotide is administered from about 2-10 times a day. For example, defibrotide may be administered in about 2, about 3, about 4, about 5, about 6, about 7, about 8, about 9, or in about 10 doses per day. In particular embodiments, the defibrotide is administered about every six hours.

In some embodiments, defibrotide administration begins on the day before the first day of conditioning (e.g. lymphodepletion). In some embodiments, defibrotide administration begins before the first day of conditioning (e.g. lymphodepletion). In certain embodiments, the one or more administrations of the defibrotide begins on or after the day a patient begins immunotherapy administration. In some embodiments, the one or more administrations of the defibrotide begins on or after the day a patient begins immunotherapy administration and continues for at least 30 days. In some embodiments, the one or more administrations of defibrotide are administered to treat CRS, CRES (i.e. CAR-T associated neurotoxicity/ICANS), or a related disorder. In some embodiments, the one or more administrations of defibrotide are administered to treat symptoms of CRS, CRES (i.e. CAR-T associated neurotoxicity/ICANS), or a related disorder. In some embodiments, the defibrotide is administered until symptoms improve. In some embodiments, the defibrotide is administered until symptoms are eradicated. In some embodiments, the defibrotide is administered until the CRS, CRES (i.e. CAR-T associated neurotoxicity/ICANS), or related disorder is cured.

In certain embodiments, defibrotide is administered prophylactically. In some embodiments, one or more administrations of defibrotide are administered prophylactically to a patient determined to be at high-risk of developing CRS, CRES (i.e. CAR-T associated neurotoxicity/ICANS), or a related disorder. In some embodiments, the one or more administrations of the defibrotide begin before administration of the immunotherapy begins. In some embodiments, the one or more administrations of the defibrotide begins at least three days before administration of the immunotherapy begins. In some embodiments, the one or more administrations of the defibrotide begins before the patient develops CRS, CRES (i.e. CAR-T associated neurotoxicity/ICANS), or a related disorder. In some embodiments, the one or more administrations of the defibrotide begins before the patient starts showing symptoms of CRS, CRES (i.e. CAR-T associated neurotoxicity/ICANS), or a related disorder. In some embodiments, the one or more administrations of the defibrotide begins after the patient shows an altered level of a biomarker associated with the development of CRS, CRES, neurotoxicity, or a related disorder. In some embodiments, prophylactic administration of defibrotide prevents the development of CRS, CRES (i.e. CAR-T associated neurotoxicity/ICANS), or a related disorder. In some embodiments, prophylactic administration of defibrotide delays the development of CRS, CRES (i.e. CAR-T associated neurotoxicity/ICANS), or a related disorder. In some embodiments, prophylactic administration of defibrotide delays or ameliorates the development of one or more symptoms of CRS, CRES (i.e. CAR-T associated neurotoxicity/ICANS), or a related disorder.

In some embodiments, the one or more defibrotide treatments may begin before the patient is diagnosed with CRS, CRES (i.e. CAR-T associated neurotoxicity/ICANS), or a related disorder. In some embodiments, the one or more defibrotide treatments may begin on the same day as the patient was diagnosed with CRS, CRES (i.e. CAR-T associated neurotoxicity/ICANS), or a related disorder or, for a variety of reason which are readily apparent to a skilled artisan, they may begin on a day after the patient was diagnosed with CRS, CRES (i.e. CAR-T associated neurotoxicity/ICANS), or a related disorder. For example, the defibrotide treatments may begin on days 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 after the patient was diagnosed as having CRS, CRES (i.e. CAR-T associated neurotoxicity/ICANS), or a related disorder. Thus, in some embodiments, the one or more administrations of the defibrotide begins on the same day that the patient diagnosed as having CRS, CRES (i.e. CAR-T associated neurotoxicity/ICANS), or a related disorder (i.e., day 0). In other embodiment, the one or more administrations of the defibrotide begins on 1, 2, 3, 4, 5, 6, or 7 days after the patient diagnosed as having CRS, CRES (i.e. CAR-T associated neurotoxicity/ICANS), or a related disorder. In some embodiments, the one or more administrations of defibrotide begin 1 day after the patient was diagnosed as having CRS, CRES (i.e. CAR-T associated neurotoxicity/ICANS), or a related disorder.

The timing of the administration of the defibrotide may depend on the particular patient (e.g. whether the patient is at high-risk of developing CRS, CRES (i.e. CAR-T associated neurotoxicity/ICANS), or a related disorder) and the type of immunotherapy to be administered or administered.

As a skilled artisan will appreciate, the defibrotide treatment period may vary on a patient-by-patient basis. In some embodiments, the defibrotide treatment period is determined by monitoring signs and symptoms of CRS, CRES (i.e. CAR-T associated neurotoxicity/ICANS), or a related disorder. For example, if the signs and symptoms of CRS, CRES (i.e. CAR-T associated neurotoxicity/ICANS), or a related disorder are still present after an initial treatment period, defibrotide treatment is continued until resolution of CRS, CRES (i.e. CAR-T associated neurotoxicity/ICANS), or a related disorder.

The defibrotide dosing may be determined by a variety of factors that will be readily apparent to a skilled artisan. In some embodiments, the dose is based on patient's baseline body weight, defined as the patient's weight prior to immunotherapy administration begins. In some embodiments, defibrotide is administered in an amount of about 1 to about 100 mg per kilogram of body weight per day. For example the defibrotide is administered in an amount of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg per kilogram of body weight per day. In some embodiments, defibrotide is administered in an amount of about 25 mg per kilogram of body weight per day. In some embodiments, doses based on the patient's body weight were rounded to the nearest 10 mg for patients over 35 kg. In some embodiments, doses based on the patient's body weight were rounded to the nearest 5 mg for patients under 35 kg. In some embodiments, the dose is 2.5 mg/kg/dose. In some embodiments, the dose is 6.25 mg/kg/dose.

The defibrotide may be administered by any suitable route, including without limitation parenteral (e.g., intravenous, subcutaneous, intrasternal, intramuscular, or infusion techniques), oral, sublingual, buccal, intranasal, pulmonary, topical, transdermal, intradermal, mucosal, ocular, optic, rectal, vaginal, intragastric, intrasynovial, and intra-articular routes. In some embodiments, defibrotide is administered intravenously. In some embodiments, defibrotide is administered via intravenous infusion. In some embodiments, defibrotide is administered by constant intravenous infusion over a 2-hour period. In some embodiments, the defibrotide is diluted prior to infusion. In some embodiments, the diluted defibrotide solution is administered using an infusion set equipped with a filter (e.g., a 0.2 micron in-line filter). In certain embodiments, the intravenous administration line (e.g., peripheral or central) is flushed immediately before and after administration (e.g., with 5% Dextrose Injection, USP or 0.9% Sodium Chloride Injection, USP).

Any combination of the foregoing embodiments may be used in treating the patient with defibrotide. Accordingly, in some embodiments, the patient is administered defibrotide intravenously in an amount of about 6.25 mg per kilogram of body weight about every 6 hours. In some embodiments, the patient is administered defibrotide intravenously in an amount of about 6.25 mg per kilogram of body weight about every 6 hours given as a 2-hour intravenous infusion. In some embodiments, the patient is administered defibrotide intravenously in an amount of about 6.25 mg per kilogram of body weight about every 6 hours given as a constant 2-hour intravenous infusion.

In some embodiments, the defibrotide is administered subcutaneously. In some embodiments, the defibrotide is administered subcutaneously by means of a device that is commercially available such as, for example, the FREE-DOM60® pump or similar (RMS™ Medical Products). In some embodiments, the defibrotide is administered subcutaneously using an automated injection device. Subcutaneous administration of a high concentration low viscosity defibrotide formulation via an automated injection device may offer significant reduction of the time for clinical administration and enable outpatient dosing of the product for as long as needed. The use of an automated injection device improves convenience and allows faster administration by health-care professionals (HCP), care-givers, or even self-administration by the patients.

In some embodiments, the route of administration affects the efficacy and/or longevity of the formulations of the present disclosure. In some embodiments, subcutaneous, intramuscular and/or intraperitoneal administration is associated with an extended systemic half-life compared to the same formulation administered intravenously. In some embodiments, subcutaneous administration of the formulation provides lower peak-to-trough ratios of plasma concentrations compared to the same formulation administered intravenously. In some embodiments, subcutaneous administration provides improved efficacy and/or improves the safety profile of the formulation compared to the same formulation administrated intravenously.

Devices for subcutaneous administration may be prefilled, with for example a predefined adult or pediatric dose, or may be used to administer a weight-based dose specific for individual patients. In some embodiments, the patient determines the dose and administers it. In some specific embodiments, formulations of the disclosure are administered subcutaneously in less than about two hours, less than about one hour, or less than about 30 minutes. In some specific embodiments, formulations of the disclosure are delivered subcutaneously over about 5 minutes to about 1 hour, about 10 minutes to about 1 hour or about 15 minutes to about 45 minutes.

The formulation dosing may be determined by a variety of factors that will be readily apparent to a skilled artisan. In some embodiments, the dose is based on patient's baseline body weight. In some embodiments, formulation is administered in an amount of about 1 to about 100 mg per kilogram of body weight per day. For example the formulation is administered in an amount of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg per kilogram of body weight per day. In some embodiments, formulation is administered in an amount of about 25 mg per kilogram of body weight per day. In some embodiments, doses based on the patient's body weight are rounded to the nearest 10 mg for patients over 35 kg. In some embodiments, doses based on the patient's body weight were rounded to the nearest 5 mg for patients under 35 kg.

The formulation may be administered as a single daily dose or in multiple doses per day. In some embodiments, formulation is administered once a day. In some embodiments, formulation is administered in multiple doses per day. For example, the formulation may be administered in 2, 3, 4, 5, 6, 7, 8, 9, or in 10 doses per day. In some embodiments, the formulation is administered in four doses per day. In some embodiments, the formulation is administered in four doses per day every 6 hours.

In some embodiments, subcutaneous administration of the low-viscosity formulations of the present disclosure allows for less-frequent administration and/or lower doses. In some embodiments, subcutaneous administration of the low-viscosity formulation of the present disclosure allows for reduced administration volume.

In some embodiments, administration of defibrotide prevents, delays, treats, or ameliorates development of CRS, CRES (i.e. CAR-T associated neurotoxicity/ICANS) or related disorders and/or symptoms thereof compared to an untreated patient or the same patient before defibrotide administration. In some embodiments, CRS, CRES (i.e. CAR-T associated neurotoxicity/ICANS), or related disorders and/or symptoms thereof are prevented, delayed, treated, or ameliorated in the patient between day 1 and year 10. In some embodiments, administration of defibrotide prevents, delays, treats, or ameliorates development of CRS, CRES (i.e. CAR-T associated neurotoxicity/ICANS), or related disorders and/or symptoms thereof compared to an untreated patient or the same patient before defibrotide administration at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of defibrotide prevents, delays, treats, or ameliorates development of CRS, CRES (i.e. CAR-T associated neurotoxicity/ICANS), or related disorders and/or symptoms thereof compared to an untreated patient or the same patient before defibrotide administration for about 1 day, about 1 week, about 1 month, about 2 months, about 3 months, about 4 months, about 5 months, about 6 months, about 1 year, about 2 years, about 5 years, or about 10 years, or more.

In some embodiments, administration of defibrotide prevents, delays, treats, or ameliorates CRS, CRES, or related disorders and/or symptoms thereof by about 1%, about 5%, about 10%, about 20%, about 30%, about 40%, about 50%, about 60%, about 70%, about 80%, about 90%, or about 100% compared to an untreated patient or the same patient before defibrotide administration. In some embodiments, administration of defibrotide prevents, delays, treats, or ameliorates development of CRS, CRES (i.e. CAR-T associated neurotoxicity/ICANS), or related disorders and/or symptoms thereof compared to an untreated patient or the same patient before defibrotide administration by about 1%, (i.e. CAR-T associated neurotoxicity/ICANS) about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of defibrotide prevents, delays, treats, or ameliorates development of CRS, CRES (i.e. CAR-T associated neurotoxicity/ICANS), or related disorders and/or symptoms thereof compared to an untreated patient or the same patient before defibrotide administration by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more.

In some embodiments, administration of defibrotide modulates the expression biomarkers associated with CRS, CRES (i.e. CAR-T associated neurotoxicity/ICANS), or related disorders compared to an untreated or the same patient before defibrotide administration. In some embodiments, administration of the defibrotide decreases expression levels of biomarkers associated with CRS, CRES (i.e. CAR-T associated neurotoxicity/ICANS), or related disorders compared to an untreated patient or the patient after diagnosis with CRS, CRES (i.e. CAR-T associated neurotoxicity/ICANS), or a related disorder. In some embodiments, administration of the defibrotide decreases serum levels of biomarkers associated with CRS, CRES (i.e. CAR-T associated neurotoxicity/ICANS), or related disorders compared to an untreated patient or the patient after diagnosis with CRS, CRES (i.e. CAR-T associated neurotoxicity/ICANS), or a related disorder. In some embodiments, the biomarker is associated with CRS and/or CRES (i.e. CAR-T associated neurotoxicity/ICANS). These CRS and/or CRES associated biomarkers include, but are not limited to, IL1-Rα, IL-6, IL-6R, soluble IL-6R, soluble gp130, IFNα, IFNγ, IL-15, IL-8, IL-2, sIL2Ra, IL8, IP10, MCP1, MIG, GM-CSF, TNFα, MIP-1α, MIP1β and IL-10, or a combination thereof. In some embodiments, the biomarker is associated with neurotoxicity. In some embodiments, these neurotoxicity-associated biomarkers include, but are not limited to, MAO and ChE enzyme activity, D2 receptor, mACh receptor, Hsp70, autoantibodies, c-fos expression, ornithine decarboxylase gene expression, cerebrospinal fluid markers, and/or plasma components (e.g. myelin basic protein, anti-NF, anti-myelin antibody, anti-GFAP antibody, anti-nerve growth factor antibody), IFNg, TNFRp55, Endothelin-1, soluble Vascular Cell Adhesion Molecule (VCAM), Intra-Cellular Adhesion Molecule (ICAM), E-selectin, soluble Thrombomodulin, Von Willebrand factor (vWF), DAMP (damage-associated molecular patterns), and PAMP (pathogen-associated molecular patterns) or a combination thereof.

In some embodiments, biomarkers expression associated with CRS, CRES (i.e. CAR-T associated neurotoxicity/ICANS) or related disorders is modulated in the patient between day 1 and year 10. In some embodiments, administration of defibrotide modulates biomarkers associated with CRS, CRES (i.e. CAR-T associated neurotoxicity/ICANS), or related disorders compared to an untreated patient or the same patient before defibrotide administration at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of defibrotide modulates the expression of biomarkers associated with CRS, CRES (i.e. CAR-T associated neurotoxicity/ICANS) or related disorders compared to an untreated patient or the same patient before defibrotide administration for about 1 day, about 1 week, about 1 month, about 2 months, about 3 months, about 4 months, about 5 months, about 6 months, about 1 year, about 2 years, about 5 years, or about 10 years, or more.

In some embodiments, administration of defibrotide modulates expression of biomarkers associated with CRS, CRES (i.e. CAR-T associated neurotoxicity/ICANS), or related disorders by about 1%, about 5%, about 10%, about 20%, about 30%, about 40%, about 50%, about 60%, about 70%, about 80%, about 90%, or about 100% compared to an untreated patient or the same patient before defibrotide administration. In some embodiments, administration of defibrotide modulates expression of biomarkers associated with CRS, CRES (i.e. CAR-T associated neurotoxicity/ICANS), or related disorders compared to an untreated patient or the same patient before defibrotide administration by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of defibrotide modulates the expression of biomarkers associated with CRS, CRES (i.e. CAR-T associated neurotoxicity/ICANS), or related disorders compared to an untreated patient or the same patient before defibrotide administration by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more.

In some embodiments, the present disclosure provides methods of determining a patient population for administration of defibrotide. In some embodiments, the patient is receiving, or is about to receive an immunotherapy. In some embodiments, the patient is determined to be at high-risk of developing CRS, CRES (i.e. CAR-T associated neurotoxicity/ICANS) or a related disorder. In some embodiments, the high-risk patient group may include, but is not limited to, those with bulky disease, co-morbidities, and those who develop early onset CRS within three days of cell infusion.

In some embodiments, the patient selected for administration with defibrotide has high serum levels or increased expression of biomarkers associated with development of CRS, CRES (i.e. CAR-T associated neurotoxicity/ICANS), or a related disorder after CAR-T cell infusion and/or bispecific antibody administration. In some embodiments, the patient selected for administration with defibrotide has high serum levels or increased expression of cytokines such as IL1-Rα, IL-6, IL-6R, soluble IL-6R, soluble gp130, IFNα, IFNγ, IL-15, IL-8, IL-2, sIL2Ra, IL8, IP10, MCP1, MIG, GM-CSF, TNFα, MIP-1α, MIP1β, IL-10, MAO and ChE enzyme activity, D2 receptor, mAch receptor, Hsp70, autoantibodies, c-fos expression, ornithine decarboxylase gene expression, cerebrospinal fluid markers, and/or plasma components (e.g. myelin basic protein, anti-NF, anti-myelin antibody, anti-GFAP antibody, anti-nerve growth factor antibody), IFNg, TNFRp55, Endothelin-1, soluble Vascular Cell Adhesion Molecule (VCAM), Intra-Cellular Adhesion Molecule (ICAM), E-selectin, soluble Thrombomodulin, Von Willebrand factor (vWF), DAMP (damage-associated molecular patterns), and PAMP (pathogen-associated molecular patterns) or a combination thereof either before or one day after CAR-T cell infusion and/or bispecific antibody administration. In some embodiments, the presence of biomarkers associated with development of CRS, CRES (i.e. CAR-T associated neurotoxicity/ICANS) or a related disorder after CAR-T cell infusion and/or bispecific antibody administration is used to diagnose a patient with CRS, CRES (i.e. CAR-T associated neurotoxicity/ICANS) or a related disorder. In some embodiments, the diagnosis of a patient with CRS, CRES (i.e. CAR-T associated neurotoxicity/ICANS) or a related disorder prompts the initiation of defibrotide treatment. In some embodiments, defibrotide is administered until the serum levels or expression of one or more biomarkers associated with CRS, CRES (i.e. CAR-T associated neurotoxicity/ICANS) or a related disorder decrease compared to levels at or around the time of diagnosis. In some embodiments, defibrotide is administered until the serum levels or expression of one or more biomarkers associated with CRS, CRES (i.e. CAR-T associated neurotoxicity/ICANS), or a related disorder decrease to levels observed in patients without CRS, CRES (i.e. CAR-T associated neurotoxicity/ICANS), or a related syndrome. In some embodiments, defibrotide is administered until the serum levels or expression of one or more biomarkers associated with CRS, CRES (i.e. CAR-T associated neurotoxicity/ICANS), or a related disorder decrease to levels observed in the same patient before immunotherapy.

In accordance with some embodiments of the present disclosure, the patient is from about 0 years of age to about 16 years of age, including all ranges and subranges therein. For example, the patient is from about 0 months, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years, 11 years, 12 years, 13 years, 14 years, 15 years, to about 16 years of age. In some embodiments, the patient is from about 0 months to about 23 months of age. In some embodiments, the patient is from about 2 years to about 11 years of age. In some embodiments, the patient is from about 12 years to about 16 years of age.

In accordance with some embodiments of the present disclosure, the patient may be a pediatric patient or adult. A pediatric patient is from about 0 years of age to about 16 years of age, including all ranges and subranges therein. For example, the pediatric patient is from about 0 months, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years, 11 years, 12 years, 13 years, 14 years, 15 years, to about 16 years of age. In some embodiments, the patient is from about 0 months to about 23 months of age. In some embodiments, the patient is from about 2 years to about 11 years of age. In some embodiments, the patient is from about 12 years to about 16 years of age. An adult patient is older than 16 years of age.

The patient of the present disclosure may have a variety of underlying primary diseases. Examples of primary diseases the patient of the present disclosure may have, include but are not limited to: acute lymphoblastic leukemia, acute myeloid leukemia, adrenocortical carcinoma, kaposi sarcoma, lymphoma, anal cancer, appendix cancer, central nervous system cancer, basal cell carcinoma, bile duct cancer, bladder cancer, ewing sarcoma, osteosarcoma, malignant fibrous histiocytoma, brain stem glioma, cancerous brain tumors, such as brain stem glioma, craniopharyngnioma, and ependymoma, breast cancer, bronchial tumors, Burkitt lymphoma, carcinoid tumors, including gastrointestinal carcinoid tumors, cancerous cardiac tumors, embryonal tumors, germ cell tumors, primary lymphoma, cervical cancer, chronic lymphocytic leukemia, chronic myelogenous leukemia, chronic myeloproliferative disorders, colon cancer, colorectal cancer, cutaneous T-cell lymphoma, bile duct cancer, ductal carcinoma, endometrial cancer, ependymoma, esophageal cancer, esthesioneuroblasoma, Ewing sarcoma, extracranial germ cell tumor, extraganodal germ cell tumor, extrahepatic bile duct cancer, cancers of the eye, such as intraocular melanoma and retinoblastoma, fibrous histiocytoma of bone, gallbladder cancer, gastric cancer, gastrointestinal carcinoid tumor, gastrointestinal stroma tumors (GIST), germ cell tumors, including central nervous system, extracranial, extragonadal, ovarian, and testicular, gestational trophoblastic disease, glioma, hairy cell leukemia, head and neck cancer, heart cancer, hepatocellular (liver) cancer, histiocytosis of Langerhans cell, Hodgkin's lymphoma, hypopharyngeal cancer, islet cell tumors, pancreatic neuroendocrine tumors, kidney cancers, such as renal cell cancers and Wilms tumors, Langerhans cell histiocytosis, laryngeal cancer, leukemia, such as acute lymphoblasitc leukemia, acute myeloid leukemia, chronic lymphocytic leukemia, chronic myelogenous leukemia, and hairy cell leukemia, lip and oral cavity cancers, liver cancers, lobular carcinoma in situ, lung cancers, such as non-small cell and small cell lung cancers, lymphomas, including AIDS-related, Burkitt lymphoma, non-Hodgkin's lymphoma, cutaneous T-cell, Hodgkin's lymphoma, primary central nervous system, Waldenstrom macroglobulinemia, male breast cancer, melanoma, Merkel cell carcinoma, malignant mesothelioma, metastatic squamous neck cancer, midline tract carcinoma, such as those involving the NUT gene, mouth cancer, multiple endocrine neoplasia syndromes, multiple myeloma/plasma cell neoplasm, mycosis fungoides, myelodyplastic syndromes, myelodyplasitc/myeloproliferative neoplasms, myelogenous leukemia, either chronic or acute, myeloma, myeloproliferative disorders, nasal cavity and paranasal sinus cancer, nasopharyngeal cancer, neuroblastoma, oral cancer, oral cavity cancer, such as lip and oraopharyngeal cancer, ovarian cancer, such as epithelial, germ cell tumor, and low malignant potential tumors of the ovaries, pancreatic cancer, such as pancreatic neuroendocrine tumors (Islet cell tumors), papillomatisis, paragangioma, paranasal sinus and nasal cavity cancer, parathyroid cancer, penile cancer, pharyngeal cancer, pheochromocytoma, pituitary tumors, plasma cell neoplasms, multiple myeloma, pleuropulmonary blastoma, pregnancy and breast cancer, primary central nervous system (CNS) lymphoma, prostate cancer, rectal cancer, renal cell (kidney) cancer, renal pelvis and ureter cancers, retinoblastoma, rhabdomysarcoma, salivary gland cancer, sarcomas, such as Ewing, Kaposi, osteosarcoma, soft tissue, and uterine, Seazary syndrome, skin cancers, such as melanoma, Merkel cell carcinoma, small cell lung cancer, small intestine cancer, soft tissue sarcoma, squamous cell carcinoma, stomach (gastric) cancers, cutaneous T-cell lymphoma, testicular cancer, throat cancer, thymoma and thymic carcinomas, thyroid cancer, transitional cell cancer of the renal pelvis and ureter, carcinomas of unknown primary origin, unusual cancers of childhood, urethral cancer, uterine cancer, uterine sarcoma, vaginal cancer, vulvar cancer Waldenstrom macroglobuloma, and Wilms tumors.

In certain embodiments, patients undergoing CAR-T therapy may have undergone or be undergoing allogenic or autologous CAR-T therapy. In some embodiments, the patient of the present disclosure has undergone allogenic CAR-T therapy. In some embodiments, the patient of the present disclosure has undergone autologous CAR-T therapy.

In certain embodiments, patients being prepared for CAR-T therapy may be prepared for allogenic or autologous CAR-T therapy. In some embodiments, the patient of the present disclosure is being prepared for allogenic CAR-T therapy. In some embodiments, the patient of the present disclosure is being prepared for autologous CAR-T therapy.

In some embodiments, the patient is undergoing, or about to undergo, bispecific antibody treatment. In some embodiments, the bispecific antibody is an immunotherapeutic bispecific antibody. In some embodiments, the bispecific antibody is an anti-cancer bispecific antibody.

The following example further illustrates various embodiments of the present disclosure, but should not be construed in any way as limiting its scope.

EXAMPLES

Example 1- Defibrotide to Prevent the Development of Chimeric Antigen Receptor (CAR)-T-Cell-Associated Neurotoxicity and/or CRS The overall goal of management is to maximize the benefit from CAR-T therapy while minimizing the risk of life-threatening complications. Though in many report suggests that CRS and CRES (or CAR-T associated neurotoxicity/ICANS) are mostly reversible, monitoring of these condition requires high level of medical care and prolonged inpatient hospital stay, and though rare, mortality. While accurate assessment and prompt management of toxicities can mitigate the adverse outcomes associated with these potentially curative immunotherapies, developing a safe and effective way of preventing CRS and CRES (or CAR-T associated neurotoxicity/ICANS), without compromising the therapeutic effect would be desired.

CRS and CRES (or CAR-T associated neurotoxicity/ICANS) are associated with endothelial activation and damages, which may exist even before lymphodepletion, and exacerbated by lymphodepletion chemotherapy and/or the cytokine activation by CAR-T expansion. The use of defibrotide can contribute to the stabilization of endothelial cells, minimizes endothelial damage during the patient's treatment with CAR-T therapy, and can thereby prevent severe CRS and CRES (or CAR-T associated neurotoxicity/ICANS).

Patients

The target patient population is subjects with relapsed or refractory Diffuse Large B cell Lymphoma (DLBCL) receiving Axicabtagene ciloleucel (or Axi-cel; marketed as Yescarta®) or tisagenlecleucel for refractory or relapsed B-ALL.

Correlative analysis includes serum cytokine levels including ANG2 and vWF levels. Serum is also collected for biomarker analysis including markers of endothelial damage and activation. They are to be collected before and during CART therapy.

Clinical Phase 2 Trial:

A multicenter, open-label, single-arm, study is conducted to assess the safety and efficacy of defibrotide for the prevention of chimeric antigen receptor-T-cell (CAR-T)-associated neurotoxicity.

Figure 9:
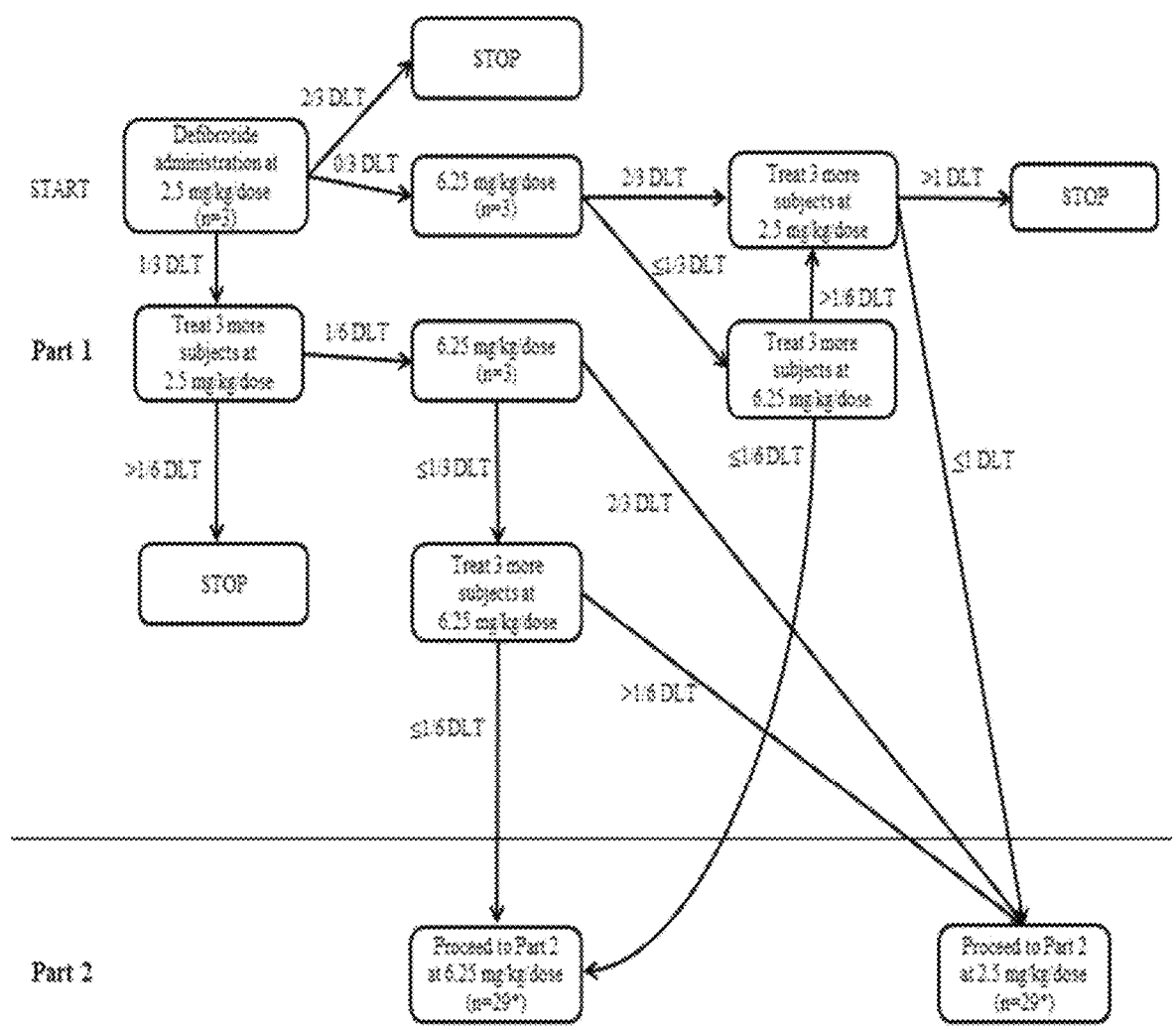
FIG. 9 shows the dose escalation algorithm used for a Phase 2 study evaluating the safety and efficacy of defibrotide for the prevention of CAR-T-associated neurotoxicity in subjects with relapsed or refractory diffuse large B-cell lymphoma (DLBCL) receiving axicabtagene ciloleucel (Yescarta®).

This is a 2-part study consisting of a low-dose safety lead-in phase (Part 1) that will determine the final treatment dose to be used in all subsequent eligible subjects (Part 2) to enroll a total of about 32 subjects at the final treatment dose. Part 1 (lead-in phase) is based on a standard 3+3 design and evaluates a 2.5 mg/kg/dose regimen of defibrotide in 3-6 eligible subjects before escalating to a 6.25 mg/kg/dose regimen in 3-6 eligible subjects according to the algorithm in FIG. 9. After the Safety Assessment Committee (SAC) establishes the recommended phase 2 dose (RP2D) based on dose-limiting toxicities (DLTs) during Part 1 of the study, Part 2 enrolls subjects at the RP2D to obtain a total of about 29 efficacy evaluable subjects, including subjects in Part 1 who were treated at the RP2D. Subjects treated at the RP2D in Part 1 will be included in the efficacy and safety analyses. The SAC will continue to monitor safety data, including serious and Grade 3 or greater treatment-emergent serious adverse events (TEAEs) throughout Part 2 of the study. Approximately 10% of enrolled subjects may not receive CAR-T treatment (Yescarta®) and, therefore, will not contribute to the primary efficacy analysis.

The Efficacy Evaluable Analysis Set includes:
All subjects receiving at least 18 doses (of all 35) of defibrotide and either
developed CAR-T-associated neurotoxicity on or before CAR-T Day +30; OR
completed the CAR-T Day +30 neurological assessment
AND
All subjects who discontinued treatment due to post-CAR-T-associated neurotoxicity before receiving 18 doses of defibrotide.

In addition, subjects whose Yescarta® infusion is delayed by more than 2 days from the original schedule are considered not evaluable for efficacy. See FIG. 9 for an outline of the Dose Escalation Algorithm. *Efficacy evaluable; subjects in Part 1 treated at the RP2D will be included in the efficacy and safety analyses.

The test product used is Defibrotide (Defitelio) Intravenous solution 200 mg/2.5 mL (80 mg/mL) vial. Study Day 1 is defined as the day of the first defibrotide infusion. In this protocol, the schedule of procedures and assessments will also reference the day relative to the day of CAR-T-cell therapy (Yescarta®) infusion (CAR-T Day 0). For example, Study Day 1 of this study will also be referred to as CAR-T Day −5, whereas the day of Yescarta® infusion (CAR-T Day 0) will be referred to as Study Day 6. Yescarta® may be delayed for up to 2 days, in which case CAR-T Day 0 will correspond to Study Day 7 (1-day delay) or Study Day 8 (2-day delay).

Dose and Mode of Administration: Eligible subjects receive defibrotide (2.5 mg/kg/dose or 6.25 mg/kg/dose) infused intravenously over 2 hours (±15 min). To minimize the endothelial damage from lymphodepletion chemotherapy, defibrotide starts on the first day (CAR-T Day −5 [Study Day 1]) of lymphodepletion chemotherapy (with 1 administration of defibrotide per day) and continues for 3 days (with administration of defibrotide on each day occurring immediately prior to lymphodepletion). The window between the end of defibrotide infusion and start of lymphodepletion chemotherapy should not exceed 2 hours. On CAR-T Day −2 (Study Day 4) and CAR-T Day −1 (Study Day 5), defibrotide is not administered. Starting on CAR-T Day 0 (Study Day 6) prior to Yescarta® infusion, defibrotide is administered every 6 hours (4 times a day) until CAR-T Day +7 (Study Day 13). A minimum of 2 doses of defibrotide is administered prior to Yescarta® infusion.

Each defibrotide dose (infused over a 2 hour±15 min infusion period) is administered within ±1 hour of the scheduled dosing time provided that there is at least a 2-hour window between the end of an infusion and the start of the next infusion. Defibrotide is administered for a total of 11 days: once a day for 3 days on CAR-T Days −5, −4, −3 (Study Days 1, 2, 3) during lymphodepletion chemotherapy; no defibrotide administration on CAR-T Day −2 (Study Day 4) and CAR-T Day −1 (Study Day 5); and 4 times a day for 8 days on CAR-T Days 0 to +7 (Study Days 6 to 13). The dosing schedule is summarized in FIG. 10.

Inclusion Criteria for subjects enrolled in this study:
1. Subject is ≥18 years of age at signing of informed consent.
2. Subject has been diagnosed with relapsed or refractory DLBCL (including DLBCL not otherwise specified, primary mediastinal large B-cell lymphoma, high grade B-cell lymphoma, and DLBCL arising from follicular lymphoma) and scheduled to receive treatment with Yescarta®.
3. Female subjects of childbearing potential who are sexually active and male subjects who are sexually active and have female partners of childbearing potential agree to use a highly effective method of contraception with their partners during exposure to defibrotide and for 30 days after the last dose of defibrotide. Highly effective methods of contraception include abstinence (when this is in line with the preferred and usual lifestyle of the subject [periodic abstinence, e.g., calendar, postovulation, symptothermal methods, and withdrawal are not acceptable methods]), combined (estrogen- and progestogen-containing) hormonal contraception associated with inhibition of ovulation (i.e., birth control pills, patches, vaginal ring), progestogen-only hormonal contraception associated with inhibition of ovulation (i.e., progestin implant or injection), intrauterine device, intrauterine hormone-releasing system, surgical sterilization, and vasectomy (>6 months before CAR-T Day −5 [Study Day 1]). Surgically sterile women and men and postmenopausal women (i.e., women with >2 years of amenorrhea) do not need to use contraception.
4. Subject are able to understand and sign written informed consent.

Exclusion Criteria—Subjects who meet any of the following criteria are excluded from the study:
1. Subject is currently receiving dialysis or expected to receive dialysis.
2. Subject has used any investigational anticancer agent within 3 weeks prior to the first dose of defibrotide, or is using or plans to use any investigational agent during the study.
3. Subject has previously been treated with CAR-T therapy.
4. Hemodynamic instability requiring vasopressors or uncontrolled hypertension with persistent systolic blood pressure >180.
5. Subject has clinically significant active bleeding, history of intracranial bleeding, or is at risk for intracranial bleeding as determined by the Investigator.
6. Subject plans to use any medication that increases the risk of bleeding, including, but not limited to, systemic heparin, low molecular weight heparin, heparin analogs, alteplase, streptokinase, urokinase, antithrombin III (ATIII), oral anticoagulants including warfarin, and factor Xa inhibitors. Subjects may receive heparin (up to 100 U/kg/day) or other anticoagulants for routine central venous line management and/or intermittent dialysis or ultrafiltration.
7. Subject, in the opinion of the Investigator, is not able to comply with the study protocol, including appropriate supportive care, follow-up, research tests, and safety monitoring requirements.
8. Subject has a serious active disease or comorbid medical condition, as judged by the Investigator, that is likely to interfere with the conduct of this study.
9. Subject is pregnant or lactating and does not agree to stop breastfeeding.
10. Subject has a known history of hypersensitivity to defibrotide or any of the excipients.
11. Subject has primary central nervous system lymphoma.

Safety: the toxicity from CAR-T treatment may not be distinguishable from TEAEs attributable to defibrotide, as the safety profile of defibrotide in this subject population has not been characterized. During Part 1 of the study, all TEAEs that occur from the start of the first dose of defibrotide up to 7 days after the last dose of defibrotide are first screened for DLT by the Principal Investigator of the site where the event occurred and by the Sponsor. The final determination of DLT is then made by the SAC from TEAEs considered to have a causal relationship to defibrotide. As an exception, all bleeding TEAEs, regardless of relationship to defibrotide, will be evaluated by the SAC as potential DLTs. Because all hemorrhagic events are considered adverse drug reactions of defibrotide, the SAC focuses on any grade of intracranial hemorrhage and any other hemorrhage of Grade 2 or greater, per CTCAE v5.0. Of note, CAR-T-associated neurotoxicity is not a DLT.

Efficacy will be assessed through monitoring of subject symptoms, physical examinations, laboratory testing, imaging studies, and electroencephalography to assess neurotoxicity as needed per local standard of care and by recording survival status. Assessment of neurotoxicity will be performed by the local Investigator using the following grading systems: CTCAE v5.0 and ASBMT consensus grading system (Lee et al. 2018).

Steroid use is assessed by recording all concomitant medications used. Hospital resource is assessed by recording hospital and ICU stay days. Serial blood samples is obtained from all subjects on CAR-T Day −5 (Study Day 1), CAR-T Day 0 (Study Day 6), and CAR-T Day +7 (Study Day 13). Plasma defibrotide concentrations are measured using a validated bioanalytical method, and PK of plasma defibrotide is assessed. Serum cytokines, including markers of endothelial damage, is analyzed from serial blood samples, which is collected once daily on CAR-T Days −5 and −3 (Study Days 1 and 3) and once every other day starting from CAR-T Day 0 (Study Day 6) to discharge but not beyond CAR-T Day +14. In addition, blood collection is performed once on CAR-T Day +14 (±3 days) and on CAR-T Day +30 (±3 days), which is performed either in the hospital or as an outpatient. The DLT assessment period is from the start of the first dose of defibrotide to 7 days after the last dose of defibrotide during Part 1 of the study. In addition, through Part 1 and Part 2, safety is assessed through monitoring of adverse events (AEs) and serious adverse events (SAEs) from the signing of informed consent to 30 days after the last dose of defibrotide. Other safety assessments include vital signs, physical examinations, clinical laboratory tests, and Eastern Cooperative Oncology Group performance status. Disease status of DLBCL will be assessed by modified International Working Group criteria (Cheson et al. 2016).

The primary objective of the study is to assess the efficacy of defibrotide for the prevention of CAR-T-associated neurotoxicity by CAR-T Day +30. The primary endpoint of the study is the incidence of CAR-T-associated neurotoxicity (any grade, defined by CTCAE v5.0) by CAR-T Day +30. A Simon's optimal 2-stage design is employed to test the response rate of administration with defibrotide in the target subject population (Simon 1989). The historical rate of CAR-T-associated neurotoxicity post-CAR-T-cell therapy is 64% (Neelapu et al. 2017); it is hypothesized that administration with defibrotide will reduce this incidence by half, to a CAR-T-associated neurotoxicity rate of 32% by CAR-T Day +30 (i.e., a no CAR-T-associated neurotoxicity rate of 68%). The sample size calculation is based on testing the null and alternative hypotheses with an overall 1-sided Type I error of 0.05 and a statistical power of at least 92% when the no CAR-T-associated neurotoxicity rate is ≥68%. In the first stage, 10 evaluable subjects will be accrued. If there are 4 or fewer subjects without CAR-T-associated neurotoxicity post-CAR-T-cell therapy in these 10 subjects, the study will be stopped. Otherwise, 19 additional evaluable subjects will be accrued for a total of 29. The null hypothesis will be rejected if 15 or more subjects without CAR-T-associated neurotoxicity post-CAR-T-cell therapy are observed in these 29 subjects. Estimation of the no CAR-T-associated neurotoxicity rate will use the method of Koyama and Chen (Koyama & Chen 2008), which incorporates the 2-stage design. The corresponding confidence interval and the p-value will also be calculated using the method of Koyama and Chen. A sensitivity analysis will be performed for the primary efficacy endpoint using all enrolled subjects treated at the RP2D.

Secondary Endpoints:
Efficacy
Incidence of CAR-T-associated neurotoxicity of Grade 3 or greater defined by CTCAE v5.0 by CAR-T Day +30
Incidence of CAR-T-associated neurotoxicity (any grade and Grade 3 or greater) according to the American Society for Blood and Marrow Transplantation (ASBMT) consensus grading system (Lee et al. 2018) by CAR-T Day +30
Incidence of cytokine release syndrome (CRS; any grade, according to ASBMT consensus grading system [Lee et al. 2018]) by CAR-T Day +30
Use of high dose steroid by CAR-T Day +30

Safety
Incidence of treatment-emergent adverse events (TEAEs) that occur up to 30 days after the last dose of defibrotide
Incidence of treatment-emergent serious adverse events (TESAEs) that occur up to 30 days after the last dose of defibrotide
Lymphoma response evaluation by Cheson criteria (Cheson et al. 2016) up to CAR-T Day +60

Pharmacokinetics (PK):
PK of defibrotide

Exploratory Endpoints:
Biomarker analysis before and after defibrotide
Biomarker analysis before and after Yescarta
Duration of hospital stay and intensive care unit (ICU) stay

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

This application incorporates by reference the following publications, patents and applications in their entireties for all purposes: U.S. application Ser. No. 16/105,319 filed Aug. 3, 2018; 62/776,500 filed Dec. 7, 2018 and 62/802,099 filed Feb. 6, 2019; as well as U.S. Pat. Nos. 3,770,720, 3,829,567, 3,899,481, 4,649,134, 4,693,995, 4,938,873, 4,985,552, 5,081,109, 5,116,617, 5,223,609, 5,646,127, 5,646,268, and 6,046,172.

REFERENCES

1. Neelapu et al. 2018 Nature Review in Clinical Oncology
2. Maude, S L, Laetsch T W, Buechner J, et al. Tisagenlecleucel in Children and Young Adults with B-Cell Lymphoblastic Leukemia. N Engl J Med. 2018; 378:439-448.
3. Neelapu S S, Locke F L, Bartlett N L, et al. Axicabtagene Ciloleucel CAR T-Cell Therapy in Refractory Large B-Cell Lymphoma. N Engl J Med. 2017; 377:2531-2544.
4. Park J H, Riviere I, Gonen M, et al. Long-Term Follow-up of CD19 CAR Therapy in Acute Lymphoblastic Leukemia. N Engl J Med. 2018; 378:449-459.
5. Sadelain M, Brentjens R, Riviere I. The basic principles of chimeric antigen receptor design. Cancer Discov. 2013; 3:388-398.
6. Brudno J N, Kochenderfer J N. Toxicities of chimeric antigen receptor T cells: recognition and management. Blood. 2016; 127:3321-3330.
7. Hu Y, Sun J, Wu Z, et al. Predominant cerebral cytokine release syndrome in CD19-directed chimeric antigen receptor-modified T cell therapy. J Hematol Oncol. 2016; 9:70.

8. Lee D W, Gardner R, Porter D L, et al. Current concepts in the diagnosis and management of cytokine release syndrome. Blood. 2014; 124:188-195.
9. Maude S L, Barrett D, Teachey D T, Grupp S A. Managing cytokine release syndrome associated with novel T cell-engaging therapies. Cancer J. 2014; 20:119-122.
10. Teachey D T, Lacey S F, Shaw P A, et al. Identification of Predictive Biomarkers for Cytokine Release Syndrome after Chimeric Antigen Receptor T-cell Therapy for Acute Lymphoblastic Leukemia. Cancer Discov. 2016; 6:664-679.
11. Schuster S J, Bishop M R, Tam C S, et al. Primary Analysis of Juliet: A Global, Pivotal, Phase 2 Trial of CTL019 in Adult Patients with Relapsed or Refractory Diffuse Large B-Cell Lymphoma. Blood. 2017: abstract 577.
12. Neelapu S S, Tummala S, Kebriaei P, et al. Chimeric antigen receptor T-cell therapy—assessment and management of toxicities. Nat Rev Clin Oncol. 2018; 15:47-62.
13. Maude S L, Frey N, Shaw P A, et al. Chimeric antigen receptor T cells for sustained remissions in leukemia. N Engl J Med. 2014; 371:1507-1517.
14. Kochenderfer J N, Dudley M E, Kassim S H, et al. Chemotherapy-refractory diffuse large B-cell lymphoma and indolent B-cell malignancies can be effectively treated with autologous T cells expressing an anti-CD19 chimeric antigen receptor. J Clin Oncol. 2015; 33:540-549.
15. Turtle C J, Hanafi L A, Berger C, et al. Immunotherapy of non-Hodgkin's lymphoma with a defined ratio of CD8+ and CD4+CD19-specific chimeric antigen receptor-modified T cells. Sci Transl Med. 2016; 8:355ra116.
16. Locke F L, Neelapu S S, Bartlett N L, et al. Phase 1 Results of ZUMA-1: A Multicenter Study of KTE-C19 Anti-CD19 CAR T Cell Therapy in Refractory Aggressive Lymphoma. Mol Ther. 2017; 25:285-295.
17. Lee D W, Kochenderfer J N, Stetler-Stevenson M, et al. T cells expressing CD19 chimeric antigen receptors for acute lymphoblastic leukaemia in children and young adults: a phase 1 dose-escalation trial. Lancet. 2015; 385:517-528.
18. Davila M L, Riviere I, Wang X, et al. Efficacy and toxicity management of 19-28z CAR T cell therapy in B cell acute lymphoblastic leukemia. Sci Transl Med. 2014; 6:224ra225.
19. Rose-John S. IL-6 trans-signaling via the soluble IL-6 receptor: importance for the pro-inflammatory activities of IL-6. Int J Biol Sci. 2012; 8:1237-1247.
20. Scheller J, Chalaris A, Schmidt-Arras D, Rose-John S. The pro- and anti-inflammatory properties of the cytokine interleukin-6. Biochim Biophys Acta. 2011; 1813:878-888.
21. Chen F, Teachey D T, Pequignot E, et al. Measuring IL-6 and sIL-6R in serum from patients treated with tocilizumab and/or siltuximab following CAR T cell therapy. J Immunol Methods. 2016; 434:1-8.
22. Singh J A, Beg S, Lopez-Olivo M A. Tocilizumab for rheumatoid arthritis. Cochrane Database Syst Rev. 2010: CD008331.
23. Deisseroth A, Kaminskas E, Grillo J, et al. U.S. Food and Drug Administration approval: ruxolitinib for the treatment of patients with intermediate and high-risk myelofibrosis. Clin Cancer Res. 2012; 18:3212-3217.
24. Bonifant C L, Jackson H J, Brentjens R J, Curran K J. Toxicity and management in CAR T-cell therapy. Mol Ther Oncolytics. 2016; 3:16011.
25. Zaki M H, Nemeth J A, Trikha M. CNTO 328, a monoclonal antibody to IL-6, inhibits human tumor-induced cachexia in nude mice. Int J Cancer. 2004; 111:592-595.
26. Mihara M, Kasutani K, Okazaki M, et al. Tocilizumab inhibits signal transduction mediated by both mIL-6R and sIL-6R, but not by the receptors of other members of IL-6 cytokine family. Int Immunopharmacol. 2005; 5:1731-1740.
27. Nishimoto N, Terao K, Mima T, Nakahara H, Takagi N, Kakehi T. Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease. Blood. 2008; 112:3959-3964.
28. Paliogianni F, Ahuja S S, Balow J P, Balow J E, Boumpas D T. Novel mechanism for inhibition of human T cells by glucocorticoids. Glucocorticoids inhibit signal transduction through IL-2 receptor. J Immunol. 1993; 151:4081-4089.
29. Lanza L, Scudeletti M, Puppo F, et al. Prednisone increases apoptosis in in vitro activated human peripheral blood T lymphocytes. Clin Exp Immunol. 1996; 103:482-490.
30. Franchimont D, Louis E, Dewe W, et al. Effects of dexamethasone on the profile of cytokine secretion in human whole blood cell cultures. Regul Pept. 1998; 73:59-65.
31. Ozdemir E, St John L S, Gillespie G, et al. Cytomegalovirus reactivation following allogeneic stem cell transplantation is associated with the presence of dysfunctional antigen-specific CD8+ T cells. Blood. 2002; 100:3690-3697.
32. Turtle C J, Hay K A, Hanafi L A, et al. Durable Molecular Remissions in Chronic Lymphocytic Leukemia Treated With CD19-Specific Chimeric Antigen Receptor-Modified T Cells After Failure of Ibrutinib. J Clin Oncol. 2017; 35:3010-3020.
33. Schuster S J, Svoboda J, Chong E A, et al. Chimeric Antigen Receptor T Cells in Refractory B-Cell Lymphomas. N Engl J Med. 2017; 377:2545-2554.
34. Grupp S A, Kalos M, Barrett D, et al. Chimeric antigen receptor-modified T cells for acute lymphoid leukemia. N Engl J Med. 2013; 368:1509-1518.
35. Santomasso B, Jae Hong P, Isabelle R, et al. Biomarkers associated with neurotoxicity in adult patients with relapsed or refractory B-ALL (R/R B-ALL) treated with CD19 CAR T cells. Journal of Clinical Oncology. 2017; 35:3019-3019.
36. Hovinga C A. Levetiracetam: a novel antiepileptic drug. Pharmacotherapy. 2001; 21:1375-1388.
37. Guenther S, Bauer S, Hagge M, et al. Chronic valproate or levetiracetam treatment does not influence cytokine levels in humans. Seizure. 2014; 23:666-669.
38. Johnson L A, June C H. Driving gene-engineered T cell immunotherapy of cancer. Cell Res. 2017; 27:38-58.
39. Reuters. Juno ends development of high-profile leukemia drug after deaths. http://wwwreuterscom/article/us-juno-leukemiaidUSKBN1685QQ. 2017.
40. Hay K A, Hanafi L A, Li D, et al. Kinetics and biomarkers of severe cytokine release syndrome after CD19 chimeric antigen receptor-modified T-cell therapy. Blood. 2017; 130:2295-2306.
41. Valentijn K M, Sadler J E, Valentijn J A, Voorberg J, Eikenboom J. Functional architecture of Weibel-Palade bodies. Blood. 2011; 117:5033-5043.

42. Fiedler U, Scharpfenecker M, Koidl S, et al. The Tie-2 ligand angiopoietin-2 is stored in and rapidly released upon stimulation from endothelial cell Weibel-Palade bodies. Blood. 2004; 103:4150-4156.
43. Darwish I, Liles W C. Emerging therapeutic strategies to prevent infection-related microvascular endothelial activation and dysfunction. Virulence. 2013; 4:572-582.
44. Mikacenic C, Hahn W O, Price B L, et al. Biomarkers of Endothelial Activation Are Associated with Poor Outcome in Critical Illness. PLoS One. 2015; 10: e0141251.
45. Page A V, Liles W C. Biomarkers of endothelial activation/dysfunction in infectious diseases. Virulence. 2013; 4:507-516.
46. Page A V, Tarr P I, Watkins S L, et al. Dysregulation of angiopoietin 1 and 2 in *Escherichia coli* 0157:H7 infection and the hemolytic-uremic syndrome. J Infect Dis. 2013; 208:929-933.
47. Ricciuto D R, dos Santos C C, Hawkes M, et al. Angiopoietin-1 and angiopoietin-2 as clinically informative prognostic biomarkers of morbidity and mortality in severe sepsis. Crit Care Med. 2011; 39:702-710.
48. Gust J, Hay K A, Hanafi L A, et al. Endothelial Activation and Blood-Brain Barrier Disruption in Neurotoxicity after Adoptive Immunotherapy with CD19 CAR-T Cells. Cancer Discov. 2017; 7:1404-1419.
49. Pescador R, Capuzzi L, Mantovani M, Fulgenzi A, Ferrero M E. Defibrotide: properties and clinical use of an old/new drug. Vascul Pharmacol. 2013; 59:1-10.
50. Richardson P G, Corbacioglu S, Ho V T, et al. Drug safety evaluation of defibrotide. Expert Opin Drug Saf. 2013; 12:123-136.
51. Guglielmelli T, Bringhen S, Palumbo A. Update on the use of defibrotide. Expert Opin Biol Ther. 2012; 12:353-361.
52. Corsi M, Parise M, Gaja G, Ferrero M E. Possible role of defibrotide in endothelial cell protection. Int J Tissue React. 1993; 15:157-161.
53. Palomo M, Mir E, Rovira M, Escolar G, Carreras E, Diaz-Ricart M. What is going on between defibrotide and endothelial cells? Snapshots reveal the hot spots of their romance. Blood. 2016; 127:1719-1727.
54. Cimminiello C, Milani M, Pietra A, et al. Deficient fibrinolytic response in patients with Raynaud's phenomenon and its correction with defibrotide. Semin Thromb Hemost. 1991; 17 Suppl 1:106-111.
55. Ulutin O N, Balkuv-Ulutin S, Ugur M S, Ulutin T, Ozsoy Y, Cizmeci G. The pharmacology and clinical pharmacology of defibrotide: a new profibrinolytic, antithrombotic and anti-platelet substance. Adv Exp Med Biol. 1990; 281:429-438.
56. Koehl G E, Geissler E K, Iacobelli M, et al. Defibrotide: an endothelium protecting and stabilizing drug, has an anti-angiogenic potential in vitro and in vivo. Cancer Biol Ther. 2007; 6:686-690.
57. San T, Moini H, Emerk K, Bilsel S. Protective effect of defibrotide on perfusion induced endothelial damage. Thromb Res. 2000; 99:335-341.
58. Pellegatta F, Ferrero E, Marni A, Chierchia S, Forti D, Ferrero M E. The anti-ischemic drugs defibrotide and oligotide analogously inhibit leukocyte-endothelial cell adhesion in vitro. Transpl Int. 1996; 9 Suppl 1:S420-424.
59. Carreras E. How I manage sinusoidal obstruction syndrome after haematopoietic cell transplantation. Br J Haematol. 2015; 168:481-491.
60. Carreras E, Diaz-Ricart M. The role of the endothelium in the short-term complications of hematopoietic SCT. Bone Marrow Transplant. 2011; 46:1495-1502.
61. Richardson P G, Murakami C, Jin Z, et al. Multi-institutional use of defibrotide in 88 patients after stem cell transplantation with severe veno-occlusive disease and multisystem organ failure: response without significant toxicity in a high-risk population and factors predictive of outcome. Blood. 2002; 100:4337-4343.
62. Richardson P G, Smith A R, Triplett B M, et al. Earlier defibrotide initiation post-diagnosis of veno-occlusive disease/sinusoidal obstruction syndrome improves Day +100 survival following haematopoietic stem cell transplantation. Br J Haematol. 2017; 178:112-118.
63. Richardson P G, Triplett B M, Ho V T, et al. Defibrotide sodium for the treatment of hepatic veno-occlusive disease/sinusoidal obstruction syndrome. Expert Rev Clin Pharmacol. 2018; 11:113-124.
64. Wang and Han (2018) Biomarkers of cytokine release syndrome and neurotoxicity related to CAR-T cell therapy. Biomark Res. 6:4.
65. Simon R. Optimal two-stage designs for phase II clinical trials. Control Clin Trials 1989; 10(1): 1-10.
66. Cheson B D, Ansell S, Schwartz L, et al. Refinement of the Lugano Classification lymphoma response criteria in the era of immunomodulatory therapy. Blood 2016; 128 (2): 2489-2496.
67. Lee D W, Santomasso B D, Locke F L, et al. ASBMT consensus grading for cytokine release syndrome and neurological toxicity associated with immune effector cells. Biol Blood Marrow Transplant 2018. [Epub ahead of print].
68. Koyama T, Chen H. Proper inference from Simon's two-stage designs. Stat Med 2008; 27(16): 3145-3154.
69. Schuster, S., et al., Tisagenlecleucel in Adult Relapsed or Refractory Diffuse Large B-Cell Lymphoma. N. Eng. J. Med. (2019); 380:45-56.

What is claimed is:

1. A method of preventing or treating Cytokine Release Syndrome (CRS) or an associated disorder in a patient comprising administering a therapeutically effective amount of defibrotide, wherein the patient is receiving or about to receive an immunotherapy, wherein the immunotherapy is selected from the group consisting of:
    a) lymphodepletion chemotherapy;
    b) a CAR-T therapy;
    c) a monoclonal antibody; and
    d) a bispecific antibody.

2. The method of claim 1, wherein the associated disorder is CAR-related encephalopathy syndrome (CRES), neurotoxicity, chimeric antigen receptor (CAR)-T associated neurotoxicity, immune effector cell (IEC) therapy associated neurotoxicity syndromes (ICANS).

3. The method of claim 1, wherein administration of defibrotide decreases serum biomarker levels associated with the development of CRS, CRES (or CAR-T associated neurotoxicity/ICANS), and/or neurotoxicity in the patient.

4. The method of claim 1 further comprising a step of
    determining the expression of a biomarker associated with CRS, CRES, and/or neurotoxicity in the patient
    before administering a therapeutically effective amount of defibrotide.

5. The method of claim 4, wherein defibrotide is administered to the patient until
    a) the serum biomarker levels decrease to levels observed in patients who do not develop CRS, CRES (or CAR-T associated neurotoxicity/ICANS), and/or neurotoxicity; or
    b) the serum biomarker levels decrease to levels observed in the same patient before immunotherapy treatment.

6. The method of claim 1, wherein the defibrotide is administered
   a) before the administration of the immunotherapy;
   b) at the same time as the administration of the immunotherapy; or
   c) after the administration of the immunotherapy.

7. The method of claim 2, wherein the defibrotide is administered
   a) before the development of CRS, CRES (or CAR-T associated neurotoxicity/ICANS), neurotoxicity, or symptoms thereof;
   b) after the development of CRS, CRES (or CAR-T associated neurotoxicity/ICANS), neurotoxicity, or symptoms thereof; or
   c) after the development of CRS, CRES (or CAR-T associated neurotoxicity/ICANS), neurotoxicity, or symptoms thereof and administration continues until symptoms improve.

8. The method of claim 6, wherein the defibrotide is administered
   between one and three days before administration of the immunotherapy begins.

9. The method of claim 1, wherein the defibrotide is administered
   a) at a dose between 1 mg/kg and 10 mg/kg; or
   b) at a dose of 6.25 mg/kg.

10. The method of claim 1, wherein the defibrotide is administered
    a) once a day;
    b) multiple doses per day;
    c) in two to ten doses per day;
    d) four times a day; or
    e) every six hours.

11. The method of claim 10, wherein the defibrotide is administered intravenously, every six hours at a dose of 6.25 mg/kg.

12. The method of claim 3, wherein the biomarker is selected from the group consisting of IL1-Rα, IL-6, IL-6R, soluble IL-6R, soluble gp130, IFNα, IFNγ, IL-15, IL-8, IL-2, sIL2Rα, IL8, IP10, MCP1, MIG, GM-CSF, TNFα, MIP-1α, MIP1β, IL-10, anti-neuron autoantibodies, stress proteins, MAO and ChE enzyme activity, D2 receptor, mACh receptor, Hsp70, autoantibodies, c-fos expression, ornithine decarboxylase gene expression, cerebrospinal fluid markers, plasma components, IFNg, TNFRp55, Endothelin-1, soluble Vascular Cell Adhesion Molecule (VCAM), Intra-Cellular Adhesion Molecule (ICAM), E-selectin, soluble Thrombomodulin, Von Willebrand factor (vWF), DAMP (damage-associated molecular patterns), PAMP (pathogen-associated molecular patterns), and a combination thereof.

13. The method of claim 1, wherein the defibrotide is a high concentration defibrotide formulation.

14. The method of claim 13, wherein the high concentration defibrotide formulation comprises about 80 mg/mL to about 100 mg/mL of defibrotide and 10 mM to about 34 mM sodium citrate, and is formulated for subcutaneous delivery to the patient.

15. The method of claim 12, wherein said stress proteins are heat shock proteins.

16. The method of claim 12, wherein said plasma components are myelin basic protein, anti-NF, anti-myelin antibody, anti-GFAP antibody, or anti-nerve growth factor antibody.

17. The method of claim 8, wherein administration of defibrotide continues up to 30 days.

* * * * *